US008706645B2

(12) United States Patent
Hendry, Jr.

(10) Patent No.: US 8,706,645 B2
(45) Date of Patent: Apr. 22, 2014

(54) SYSTEM AND METHOD FOR APPRAISING VALUABLE ITEMS

(76) Inventor: David W. Hendry, Jr., Oakland, CA (US)

( * ) Notice: Subject to any disclaimer, the term of this patent is extended or adjusted under 35 U.S.C. 154(b) by 1667 days.

(21) Appl. No.: 10/296,120

(22) PCT Filed: May 23, 2001

(86) PCT No.: PCT/US01/16784
§ 371 (c)(1),
(2), (4) Date: Aug. 4, 2003

(87) PCT Pub. No.: WO01/91011
PCT Pub. Date: Nov. 29, 2001

(65) Prior Publication Data
US 2004/0030565 A1    Feb. 12, 2004

Related U.S. Application Data

(60) Provisional application No. 60/206,380, filed on May 23, 2000.

(51) Int. Cl.
*G06Q 10/00* (2012.01)
(52) U.S. Cl.
USPC .......................................... 705/306; 705/500
(58) Field of Classification Search
USPC ................................. 705/306, 500
See application file for complete search history.

(56) References Cited

U.S. PATENT DOCUMENTS

| | | | | |
|---|---|---|---|---|
| 5,305,238 A | * | 4/1994 | Starr et al. | 702/176 |
| 5,911,131 A | * | 6/1999 | Vig | 705/29 |
| 5,950,178 A | | 9/1999 | Borgato | |
| 5,966,673 A | * | 10/1999 | Shannon, Sr. | 702/35 |
| 6,020,954 A | | 2/2000 | Aggarwal | |
| 6,038,554 A | | 3/2000 | Vig | |
| 6,076,155 A | * | 6/2000 | Blomgren et al. | 712/225 |
| 6,167,523 A | * | 12/2000 | Strong | 726/21 |
| 6,239,867 B1 | | 5/2001 | Aggarwal | |
| 6,243,615 B1 | * | 6/2001 | Neway et al. | 700/108 |
| 6,304,853 B1 | * | 10/2001 | Malnekoff | 705/27 |
| 6,473,164 B1 | * | 10/2002 | De Jong et al. | 356/30 |
| 6,662,192 B1 | * | 12/2003 | Rebane | 707/104.1 |
| 6,725,235 B1 | * | 4/2004 | Dyer et al. | 715/771 |
| 6,947,907 B1 | * | 9/2005 | Silverman | 705/40 |
| 2002/0184191 A1 | * | 12/2002 | Marpe et al. | 707/3 |

OTHER PUBLICATIONS (http://web.archive.org/web/20000226183308/http://bluenile.com/) 15 pages.*

(Continued)

*Primary Examiner* — Kira Nguyen
(74) *Attorney, Agent, or Firm* — Baker Hostetler LLP

(57) ABSTRACT

Systems and methods for computer appraisal of jewelry and other valuable items, such as antiques, for use in assessing sales, underwriting assessments, and claims adjustments. A user provides a description of an item (102) to be valued; elements of the provided description (102) are used in conjunction with previously-collected data (126) to classify (125) and assess the value of the item. The user may select an analysis/appraisal type and method. Gaps in required information are optionally filled using already-known data (110) by table look-upo methods or by interpolation from known ranges, and the selected analysis method is used to compete valuation and description of the item (130). Assessment options include for example valuations, appraisals, technical or aesthetic descriptions, title chains, and underwriting and insurance schedules. Optionally data supplied by the user is retained for use in future evaluations.

17 Claims, 43 Drawing Sheets

(56) References Cited

OTHER PUBLICATIONS (http://web.archive.org/web/20000229161008/www.kbb.com) 10 pages.* http://web.archive.org/web/19990125085546/http://edmunds.com/ 22 pages.*

GemNotes, by Gary Roskin, Nov. 1998 of JCK magazine (7 pages) http://www.jckonline.com/article/289330-GemNotes.php.*

* cited by examiner

SYSTEM AND METHOD FOR APPRAISING VALUABLE ITEMS

CROSS REFERENCE TO RELATED APPLICATIONS

This application claims the benefit of U.S. provisional patent application Ser. No. 60/206,380, filed May 23, 2000 and entitled System and Method for Appraising and Describing Jewelry and Other Valuable Items.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

The invention disclosed herein relates generally to systems and methods for describing valuable items. More particularly, the invention relates to data processing systems and methods for appraising and otherwise evaluating the value of and describing jewelry and other items, and for providing information relating to such items for use in analyzing insurance underwriting, claims analysis, and similar issues.

In the buying, selling, and insuring of valuable items of personal property such as jewelry, gemstones, antiques, fine china, collectibles and the like, the need for accurate appraisal frequently arises. Wide variations in legitimate value exist for what might seem to be similar items, leaving the untrained observer completely at a loss to estimate value accurately. Moreover, sellers and appraisers of such valuables sometime deliberately obscure faults, flaws, or other negative aspects, and disclose only as much information regarding the items they describe as they must. In the buying and selling of personal valuables the doctrine of caveat emptor applies vigorously.

For similar reasons insurance companies and other underwriters of valuable items of personal property must proceed cautiously in assessing the value of items for which they may be asked to write polices or evaluate claims.

It is often difficult or impossible, however, to obtain accurate appraisals for particular items at reasonable cost. The jewelry, gemstone, antique, and collectibles industries tend to be insular and closed, and the assessment of pieces an arcane or esoteric exercise. The cost of paying a knowledgeable individual to provide a reliable evaluation has tended to be so high as to preclude buyers and insurers from seeking the high-quality, detailed appraisals they need.

For example, many jewelry items are fairly valued at $10,000 or less. While this value is high enough to warrant explicit listing in insurance coverage schedules, and prudence in selecting an item for purchase, it is not generally high enough to warrant a detailed professional appraisal, prepared by a trained appraiser, which can easily cost several hundred dollars. This is particularly true from the standpoint of the insurer, who can expect to recover only small amounts in annual premiums for insured items.

Additional difficulties arise with the quality of appraisal methods. Traditionally appraisals have been conducted by the "bill of materials" method, in which a value is assessed purely on an aggregation of the values of the individual parts of a piece, by determining a value for each of the parts, based only on value by weight of the materials, weight, cut, etc., used, and adding the individual values together, with no consideration given to workmanship, source, or other less tangible factors. For example, a ring of exquisite craftsmanship, and therefore extraordinary value, assessed by the "bill of materials" approach would almost certainly be significantly undervalued.

Thus buyers have been sometimes tended to take substantial risks in making purchases, and insurance companies have been placed at risk of either substantially overcharging policyholders (and therefore losing business) or losing money on claims for underinsured properties.

Other problems related to assessment methods exist as well. For example, insurers and underwriters have long needed a low-cost, quick, reliable, and preferably automatic method and system for making appraisals, and for recalculating values or appraisals on demand—as for example at the time of a loss; or on a periodic basis, as for example at the expiration or renewal of a policy period. The value of gemstones and other valuables can fluctuate wildly from year to year, depending upon the availability and popularity of particular items. For example, several years ago blue topaz was fashionable and quite valuable. Then a process was developed for manufacturing good quality, good color topaz by irradiation, and the price fell to about $1 per carat. Similarly, several years ago the price of tanzanite was quite high, due to floods at the source in Africa which made mines inaccessible; but now the mines have been restored and the value has returned to former levels. The sheer variety of types and sizes of stones makes complicates assessments also. For example, there are probably 10,000 varieties of diamonds; the price of one particular variety of which, at one particular time, past or present, a claims adjuster needs in evaluating a particular loss.

Insurers and underwriters have also long needed an effective and efficient means for evaluating the accuracy and value of appraisals based on incomplete descriptions, and for completing the appraisals in the most useful, meaningful form possible. Traditionally appraisals received by insurers and underwriters for evaluating property for policies, etc., have tended to be incomplete, and to contain large proportions of information of dubious quality; but there has been no way for the insurer or underwriter to complete descriptions to provide meaningful appraisals, or to know how to intelligently use an appraisal which has been attempted on incomplete data. Having no alternatives, insurers and underwriters have been required to use such appraisals as is, as if full faith in the quality of the appraisal was warranted, with obvious effects on the quality of the policies and potentially disastrous effects on profit margins. It would be extremely beneficial to provide underwriters and insurers with some means of completing descriptions upon which appraisals are based, and of evaluating the quality of appraisals based on incomplete data.

Thus there exists and has long existed a need for a need for a low-cost, reliable system and method for appraising jewelry, gemstones, antiques, and other valuables, useable both for the evaluation of purchases and in the creation and underwriting of insurance policies for such items; and for evaluating insurance or other claims related to such items. There is also a need, particularly among insurers and underwriters, for such a system which provides a quick but reasonably accurate estimate of the value of such items at a given selected time, optionally with incomplete description data. There is a further need for methods and systems for quickly, reliably, and efficiently completing incomplete appraisals, and for evaluating the quality of the appraisals themselves, particularly when based on incomplete descriptions.

BRIEF SUMMARY OF THE INVENTION

It is an object of the invention to provide systems and methods for appraising jewelry, gems, antiques, collectibles, and other valuables. It is a further object of the invention to provide such methods and systems for use in evaluating purchases and in creating and underwriting insurance policies for such items, and in evaluating insurance or other claims related to such items.

It is a further object of the invention to provide systems and methods for providing quick and accurate estimates of the value of such items as of a given selected time, either current or past.

It is a further object of the invention to provide data to complete incomplete descriptions and thereby enable the completion of meaningful and useful appraisals.

It is a further object of the invention to provide methods and systems for evaluating or assessing the quality or credibility of appraisals, and in particular appraisals based in incomplete descriptions.

The invention provides such systems and methods. The invention provides data processing systems and methods for describing jewelry and other valuable items, such as antiques, gemstones, fine china, and other collectibles, for use in making appraisals, detailed descriptions, insurance underwriting assessments, claims adjustments, and the like. A user is, for example, guided by a data processing system through a series of questions, or presented with a series of form-screens to complete, with a range of suggested responses, or menus from which to select items or description elements; and answers given by the user are used, where necessary in conjunction with previously-collected data, to build an appraisable description and to appraise or otherwise assess the value of a valuable item such as a piece of jewelry. The user is prompted to select an analysis or appraisal purpose and, depending upon the purpose selected, to supply as many relevant details as possible. Gaps in required information are filled using already-known data by table look-up methods or by interpolation or extrapolation over ranges of data, and the selected analysis method is used to provide a complete assessment and description of the valuable item for the indicated purpose. Assessment purpose options include for example valuations, appraisals, technical or aesthetic descriptions, title chains, and underwriting and insurance schedules. Optionally data supplied by the user is retained for use in future evaluations, and in particular for building data bases for th provision of default data used in filling gaps in given descriptions.

In one aspect the invention provides a method, performed by a data processing system, for valuing jewelry and other valuable items. The method comprises steps of receiving one or more elements of a description of an appraisable item, using at least one of such elements in characterizing the appraisable item as a member of a class of items, accessing a data set of values associated with said class of items, and associating with the appraisable item a value for said item, the value being determined using the data set.

For example, a database comprising one or more data sets of values associated with various classes of appraisable items are maintained by a data processor or data processing system. Classes are distinguishable from each other through the use of item descriptions, the descriptions being built of sets of elements. The data processing system prompts a user to enter information pertaining to the elements, as for example by building a description through selection of elements from pull-down or other types of menus, or otherwise receives the description (for example, in batch file form); uses the description to classify the item; accesses a table of values for the item class; and establishes a value for the item. For example, a user logs on to a network site and accesses a computer system comprising a bank of data used for assessing the value of jewelry, and is presented with a series of menus or user interface screens eliciting input relating to elements useable in building a description of the jewelry. Elements comprise characteristics such as the type, size, weight, color, cut, and clarity of a stone, the material in which the stone is set, and the weight, styling, and workmanship of the setting. Once a sufficiently complete description of the item has been entered, the computer classifies the item as belonging to a particular class, e.g., a ring, bracelet, necklace, or other jewelry item (or the user enters this as another description element), or as to a particular subclass of such items, accesses a database comprising a series of formulas and/or tables of values for the jewelry class, or for individual characteristics of it, based on the entered description elements, and determines a value appropriately reflecting the worth of the item. This value is reported to the user, preferably with a summary of the entered description. The appraisal thus generated may be used in assessing a purchase, creating or underwriting an insurance policy, evaluating a loss or claim, or for any other suitable purpose.

Preferably the database, and in particular the value data set used to determine the value of the item or of particular aspects or characteristics of the item, comprises a sufficiently large range or number of unique values to cover adequately a wide range of combinations of description elements, and, where gaps in data exist value, to easily determine suitable values by interpolation or extrapolation. Data sets, including item value data sets, preferably comprise pluralities, and preferably large numbers, of values organized in tables. In computing or otherwise determining a value for a classified item, the data processing system may alternately either select a value corresponding to an item, selected from those items for which values are contained in the data base, which most closely matches the item for which the user has built a description—that is, the value may be determined by table-look up procedures such as those which are conventionally used with data sets and databases; or the system may use data values for one or more preselected items (as for example, a set of items most-closely matching the entered description) and interpolating, extrapolating, or otherwise selecting values intermediate to those stored in the data set. An optional preferred method is the use of base data values factored appropriately, for example, a per-carat weight associated with a given type, size, color, cut, and quality of stone, multiplied by the weight of the stone.

Preferably data sets used with this aspect of the invention comprise data sets established historically through such means as, for example, conventional appraisal methods, and saved for referral during later assessments. Optionally such data sets are updated by inclusion of item descriptions and values entered, assembled, or determined in accordance with the invention, to provide the most current and/or comprehensive data possible for later use.

Stated another way, in this aspect the invention provides a method for appraising jewelry and other valuable items, the method being particularly suitable for execution by a data processing system such as a suitably adapted (e.g., suitably programmed or special purpose) digital computer. The method comprises the steps of eliciting or otherwise receiving or obtaining a description of an appraisable item, characterizing the item on the basis of the description as a member of a class of items, accessing a previously collected value data set comprising a set of values associated with the class of items to which the item belongs, associating with the item a value based on the characterization of the description of the item, and reporting the value, preferably with a full description and optionally with additional information related to a selected purpose.

The received description of the valuable item may comprise all or any part of a set of items usable in assembling or completing an appraisal or description of the valuable item. As discussed herein, such descriptions may be partial or complete. In another aspect the invention provides a method, particularly suitable for execution by a suitably adapted data processing system such as a digital computer, for eliciting from a source such as a user at a local or remote input terminal a description of an item to be appraised, identifying at least one important element missing from the description so elicited, providing a default value for the missing element to complete the description, and completing an appraisal of the item on the basis of the completed description. Preferably, where an element has not been provided, or is otherwise missing from the description, the attention of the user is called to the missing item prior to provision of a default value, so that the user has an opportunity to supply the data him- or herself from other sources. For example, in a computer implemented version of the invention an empty data field could be highlighted. Optionally this aspect of the invention is used in conjunction with the first aspect.

Stated another way, this aspect of the invention provides a method comprising the steps of identifying at least one missing element from a preferred form of a received description of an item to be assessed; determining with a default element data set a default value for said missing lement; and using said default value in said characterizing.

Thus preferred embodiments of the invention comprise, in addition to value data sets, tables or other sets of descriptive elements to be used in completing descriptions of items to be assessed.

As an example of the operation of this aspect of the invention, a user might provide a partial description of a piece of antique furniture. The description might lack, for example, the identity of the manufacturer, the type of wood used in construction of the piece, or the date on which the piece was completed. Assuming that each of these data items is required for an accurate appraisal of the piece, the system, after warning the user of the missing items, consults its data sets and provides suitable default values, informs or shows the user that it has done so, and determines and reports a value for the piece.

An extremely useful extension of this aspect of the invention is assessment of the quality of the completed appraisal by assessing the importance of the missing element and/or the quality of the data supplied as a default, and reporting this assessment to the user, for use by the user in determining the use to which the appraisal should be put or the extent to which the appraisal should be relied upon. Such quality assessments may be advantageously be based, for example, on the relative importance of the missing element(s), or on the quality of the default element data set from which the missing elements were supplied. For example, an assessment of a jewel based on an unknown stone quality may be reported to the user as relatively highly untrustworthy, while an assessment which lacks only the retail or original source of a stone might be reported as more highly trustworthy.

For example, in the example described above concerning the piece of antique furniture, one or more of the items missing from the user-supplied description of the piece might be considered to be very important in ensuring the accuracy of the appraisal. The system having provided a default value for one or more such items, and the appraisal provided being therefore less certain than if a complete and reliable description had been applied, the user is provided with a warning that highly important missing information has been provided by default, and that the appraisal is therefore possibly only approximate and should accordingly be used with caution. If on the other hand only items of secondary or tertiary importance are missing from the provided description and therefore provided by the system, and all primary factors have been provided by the user, an appraisal value is reported to the user with an indication that the appraisal is uncertain but that confidence in the determined value is high. Gradations in the quality of the appraisal may be made in any required number of levels. Given the preference for many insurers and others interested in such appraisal methods, a relatively simple gradation is preferred. For example, where information critical to the appraisal was missing and provided by default, the appraisal may be labeled "highly suspect" or "critical", or merely flagged as "red". Similarly, if missing information was significant, but not critical, the appraisal might be reported as "suspect," "use with caution," or flagged as "yellow," and an appraisal based on complete description flagged as "green."

An optional and particularly useful feature of these method aspects of the invention is their ready adaptability to the automatic periodic generation or updating of previously-generated or already-existing appraisals. As mentioned above, the value of an item can for a variety of reasons vary widely over time. One aspect of the invention is the creation and maintenance of an updated database of factors associated with the value of items or characteristics of items, and the values associated therewith, both for inclusion of current data in changing conditions and for historical archiving and retrieval. Preferred systems for implementing method aspects of the invention comprise facilities for automatically, or upon instruction, accessing such a database to provide an updated or historical value for an assessed item. A preferred method according to this aspect of the invention comprises accessing a previously-established description of an appraisable item; using the description in characterizing the appraisable item as a member of a class of items; accessing a data set of values associated with the class of items; and associating with the appraisable item a value for the item, the value being determined by using the data set. Updating processes according to this aspect of the invention may be initiated automatically, as for example at a given date and time, or on an interval preselected by the user, without further user intervention; or intervention may require some user input or confirmation to proceed. For example, the user may be given a prompt by the data processing system and asked whether he/she wishes for such an automatic update to take place.

Another optional additional feature of these method aspects of the invention is the retention by systems adapted for the reception of item descriptions and/or the provision of appraisals to retain the data entered by the user for use in making future appraisals. This can be particularly advantageous where it is established that the data entered is both useful and reliable. For example, it is contemplated that systems of the type described herein will be used by reputable and established jewelers, manufacturers and dealers in jewelry, antiques, and other items, industry associations, and insurance companies and underwriters, among others. In many instances such sources will have an interest in sharing and will be able to provide complete and reliable data, including data pertaining directly to values, including values for specific, fully-described items. The retention of such information for future use is highly useful in cross checking and improving future evaluations; and optionally it is retained by the system as the system is used, for completing or updating appraisals. Optionally data retained for use in making future appraisals is reviewed by the operator of the system or the implementer of the method, or by the system itself, for accuracy, reliability, and utility.

Appraisals and other descriptions provided by the methods and systems disclosed herein are useful, for example, in creating or providing reports for proposed sales, the creation or renewal of insurance policies or the setting of insurance premiums, and in the settlement, mitigation, and adjustment of insurance or other claims. They provide or facilitate the provision of, for example, insurance-to-value ratios, schedules, and the like.

Appraisal and description methods according to the invention are well suited to use by either stand-alone or networked computers. The use of networks, for example local-area networks or wide area networks such as the Internet or the World-Wide Web, is particularly advantageous because the use of multiple input or user terminals in conjunction with one or more centralized databases or data storage facilities facilitates the gathering of large amounts of description data and therefore the accurate comparison and assessment of items. Economies in th use of computer resources, and other advantages, may also be realized by implementing programs adapted for performing or accommodating methods described herein on one or more central servers, thereby facilitating centralized processing and data manipulation.

In other aspects the invention provides data processing systems, such as suitably adapted digital computer systems, for making appraisals and implementing the methods described herein, and computer readable media storing computer program codes or other means for adapting computers or other systems for doing so. For purposes of this disclosure, a data processor is any device, such as for example a digital electronic computer, suitable for or adapted for implementation of methods of the type disclosed herein, or for accomplishing the purposes described herein.

It is important to note that except insofar as a particular order of steps of any method or process described herein is inherent, or it is otherwise stated expressly that any given combination of steps must be completed in a given order, no order to the steps of any method or process described herein is implied or required.

BRIEF DESCRIPTION OF THE DRAWINGS

The invention is illustrated in the figures of the accompanying drawings which are meant to be exemplary and not limiting, and in which like references are intended to refer to like or corresponding parts.

FIGS. 3-16 are schematic views of user interface screens for use by a data processor in valuing items according to the invention.

FIG. 4 is a screen print of a data entry field for insurance-policy related information generated by a computer program adapted to perform a preferred process for appraising jewelry and other valuable items according to the invention.

FIG. 5 is a screen print of a basic data entry and process control field generated by a computer program adapted to perform a preferred process for appraising jewelry and other valuable it ms according to th invention.

FIG. 6 is a screen print of a data entry field for information related to an insured party or personal property owner generated by a computer program adapted to perform a preferred process for appraising jewelry and other valuable items according to the invention.

FIG. 7 is a screen print of a basic data entry and process control field for eliciting a description of an appraisable item generated by a computer program adapted to perform a preferred process for appraising jewelry and other valuable items according to the invention.

FIG. 8 (comprising FIGS. 8a-8ff) is a series of screen prints of a multi-layer menu for characterizing an item of jewelry or other property generated by a computer program adapted to perform a preferred process for appraising jewelry and other valuable items according to the invention.

FIG. 9 is a screen print of a basic data entry and process control field for eliciting a description of an appraisable item generated by a computer program adapted to perform a preferred process for appraising jewelry and other valuable items according to the invention, following selection of one or more items from the menu shown in FIG. 8.

FIG. 10 (comprising FIGS. 10a-10l) is a series of screen prints of a data entry and process control field comprising menus for characterizing an item of jewelry or other property generated by a computer program adapted to perform a preferred process for appraising jewelry and other valuable items according to the invention.

FIG. 11 (comprising FIGS. 11a-11d) is a series of screen prints of a data entry and process control field comprising menus for characterizing an item of jewelry or other property generated by a computer program adapted to perform a preferred process for appraising jewelry and other valuable items according to the invention.

FIG. 12 is a screen print of a basic data entry and process control field for eliciting a description of an appraisable item generated by a computer program adapted to perform a preferred process for appraising jewelry and other valuable items according to the invention, following selection characterization of an appraisable item through use the data fields and menus shown in FIGS. 10 and 11.

FIG. 13 is a screen print of a basic data entry and process control field generated by a computer program adapted to perform a preferred process for appraising jewelry and other valuable items according to the invention.

FIG. 14 is a screen print of an appraisal report generated by a computer program adapted to perform a preferred process for appraising jewelry and other valuable items according to the invention.

FIG. 15 is a screen print of a data entry field for insurance-company related information generated by a computer program adapted to perform a preferred process for appraising jewelry and other valuable items according to the invention.

FIG. 16 is a screen print of a data entry field for producer related information generated by a computer program adapted to perform a preferred process for appraising jewelry and other valuable items according to the invention.

DETAILED DESCRIPTION OF THE PREFERRED EMBODIMENTS

Figure 1:
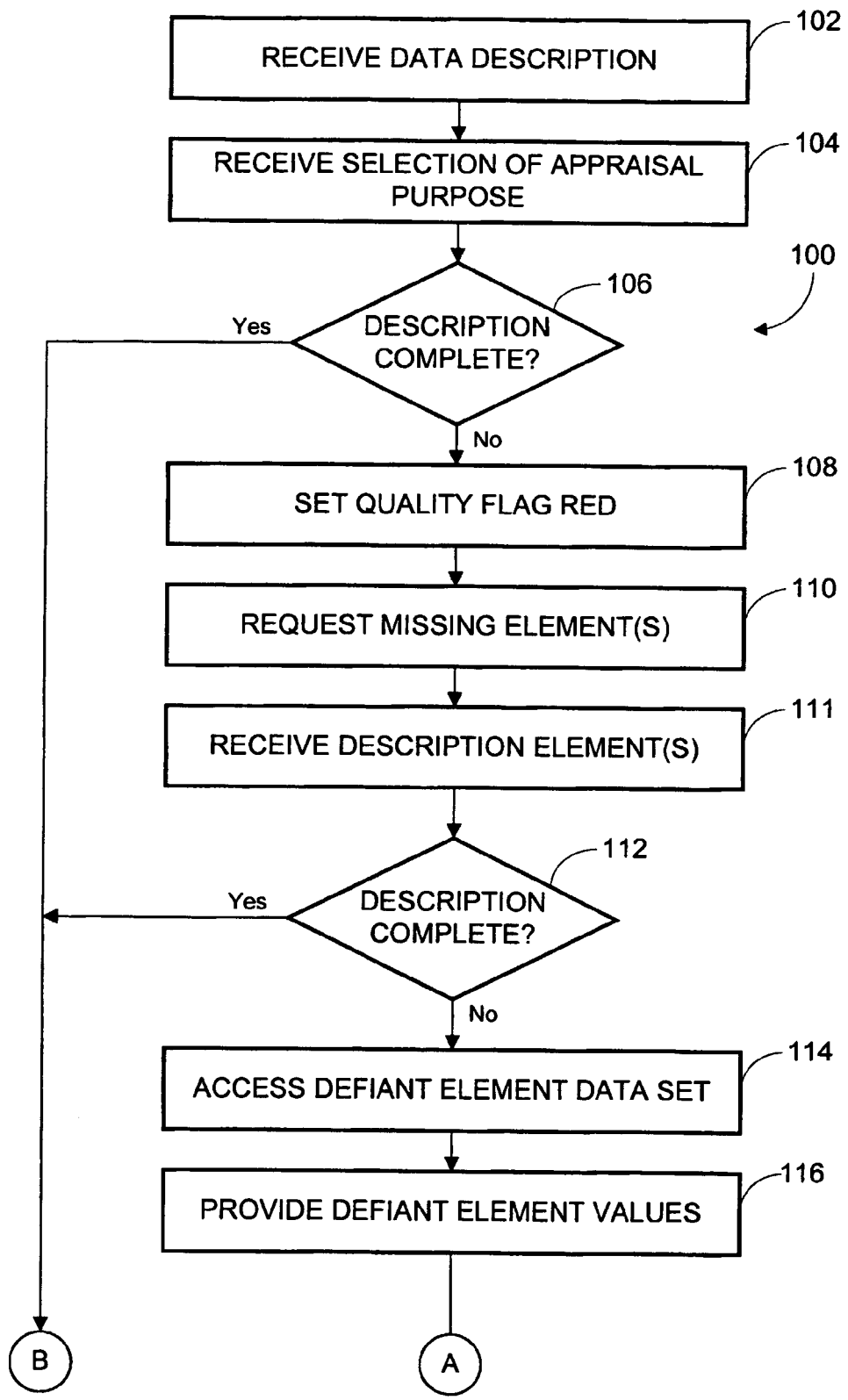
FIG. 1 is a flowchart of a preferred method for valuing items according to the invention.
Figure 1:
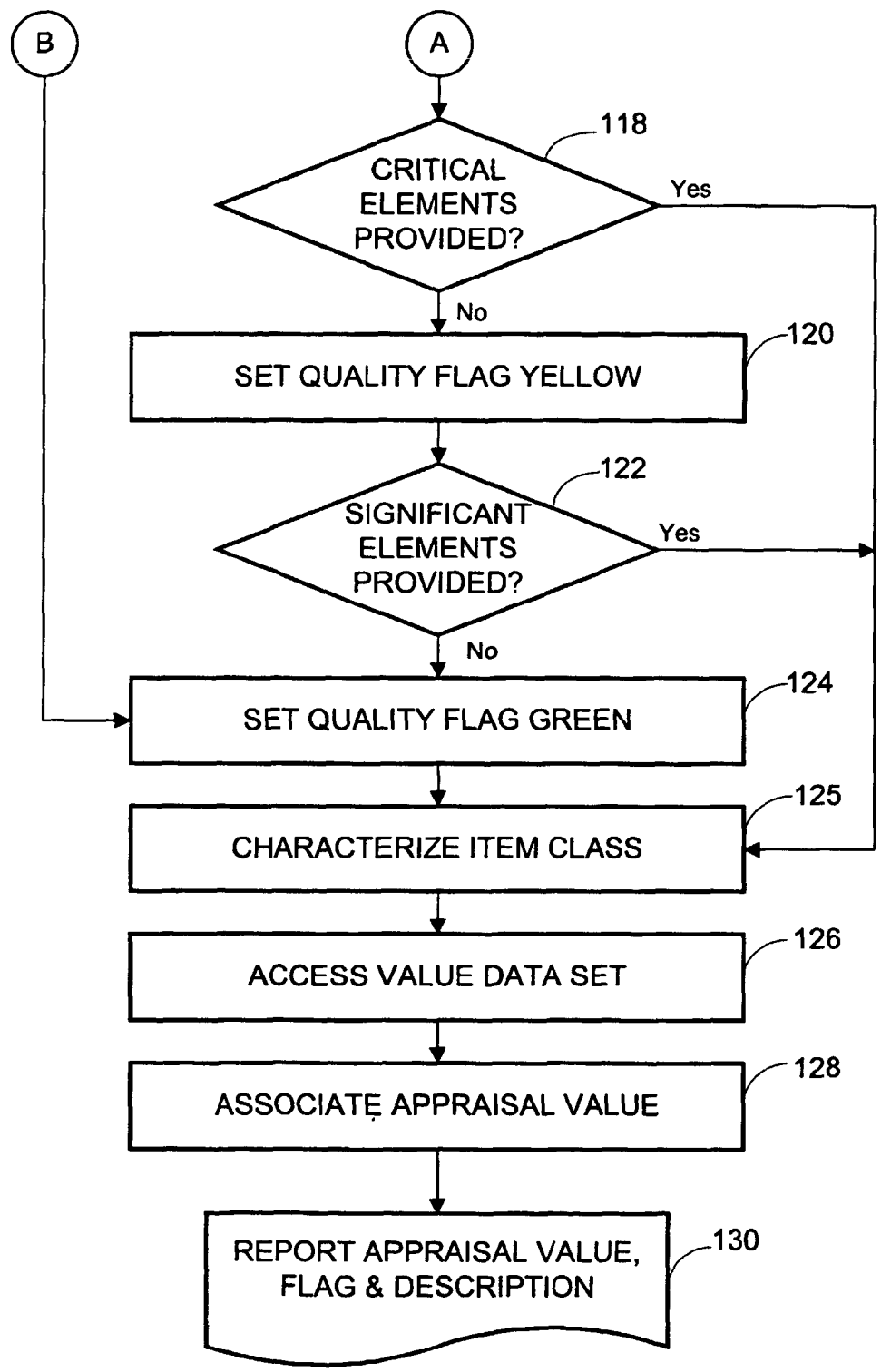

FIG. 1 is a schematic diagram of a preferred method for appraising jewelry and other valuable items according to the invention. In addition to providing a valuation of the item, the process provides for completion of an incomplete description provided by a user with missing elements, evaluation of the quality of the description provided and of the appraisal based on the description, and the best possible appraisal, given user-provided description elements and a stated purpose for the appraisal.

Process 100 begins at 102 with reception from a user of whatever information the user has concerning the item to be appraised and, at 104, of the intended purpose of the appraisal. Generally the description comprises a plurality of elements, each of which serves to help classify the item and to distinguish the item from other items in its class, thus to help determine the value of the item. For example, in the case of a jewelry appraisal the user might be asked or prompted to provide the type, weight, color, clarity and cut of the stone, and the material, weight, and style of the mounting.

As will be understood by those familiar with appraisals and other valuations of items, the value associated with an item may be influenced by the purpose of the valuation. For example, one intending to seek issuance of an insurance policy or to sell an item might wish to know a minimum accurate value of the item, in order not to underinsure it or to sell it for less than its fair market value.

At 106 the description provided by the user is assessed for completeness. If the description is complete—that is, if the description is sufficiently detailed to provide a basis for a sound valuation—the analysis is completed and a report issued that the appraisal can be used with confidence. To this end at 124 an appraisal quality flag is set to green or other appropriate value, a data set of item values is accessed at 126, and at 128 an appraisal value is determined or otherwise associated with the item. At 130 a report comprising the appraisal value, the quality flag, and a complete description of the appraised item is issued.

If the description provided by the user at 102 is not complete (that is, if the solution is not sufficiently complete to enable association of a value with the item by direct recourse to one or more data sets of item values), then at 108 an appraisal quality flag is set to red—that is, it is noted that potentially critical portions of the description are missing, and at 110 the user is requested to provide missing descriptive elements. For example, in a preferred embodiment of the invention implemented for execution on a computer, a user interface screen providing windows or data fields for entry of all required elements is presented for use by the user in entering descriptive element data. Once the user indicates that he/she has completed entry of the description, for example by selecting an item displayed on the interface screen indicating that the description entry is complete, the description is assessed for completeness. If elements required for a complete or satisfactory appraisal are missing, the attention of the user is drawn to those portions of the form screen provided for entry of the missing elements, as for example by highlighting those potions by changing their color or otherwise making them more noticeable or prominent. At the same time, the user is presented with an option of having default values supplied for missing elements and proceeding with the appraisal. At 111 any such additional elements entered by the user are received.

At 112 the description is again assessed for completeness. If the user has provided a complete description, at 124 the appraisal quality flag is reset to green, a data set of item values is accessed at 126, at 128 an appraisal value is associated with the item, and at 130 a report comprising the appraisal value, the quality flag, and a complete description of the appraised item is issued.

If the description as assessed at 112 is still incomplete, a data set of default element values is accessed at 114 and at 116 values are provided for elements missing from the description. This aspect of the process may be completed in any satisfactory manner, and optionally may be influenced by the choice indicated at 104 of the purpose for the analysis. For example, one particularly satisfactory way of providing default data values is through the use of a series of tables of appropriate values. In the jewelry example in which a complete data set comprises the type, weight, color, clarity and cut of the stone and the material, weight, and style of the mounting, one or more sets of tables for each element type is provided. A selection of types of stones, as for example, diamonds, rubies, emeralds, sapphires, and the like is provided; along with a range of weights, preferably from a small fraction of a carat to a large number of carats. Colors and cuts preferably correspond to the type of stone selected; in preferred embodiments only values consistent with and appropriate to the other values entered are accessible. For example, a "blue" stone color would not be made available in an appraisal for a ruby. Optionally different sets of tables or other data sets may be provided for different appraisal types.

The actual default value provided for a missing element may depend upon the indicated purpose of the appraisal. For example, in defining a schedule of covered items for a new policy, it may be in an insurance company's interest to provide conservative appraisals for items where doubts exist as to the characteristics of an insured item. Thus for example, if no value were entered by the user for the "cut" description, it might be in the company's best interest to assume that the item comprises a relatively rare or desirable cut, in order to ensure that adequate premiums are collected in order to protect against losses in the event of claims. This optional feature of providing different appraisal values based on the intent of the appraisal is readily accomplished by providing a range of tables and supporting logic suitable to the purpose. The selection of suitable values and the construction of suitable tables will not trouble the process designer of ordinary skill in the art, once he or she has been mad familiar with this disclosure.

Suitable default values having been provided at 116 for missing descriptive elements, a determination is made at 118 whether any of the missing elements filled by default are critical to completion of an accurate appraisal. For example, a missing stone type in the appraisal of a ring might have a marked effect on the quality of the appraisal, as the values of various stone types vary widely and, lacking other information, a guess must be made to allow the appraisal to continue. The lack of this information of this type could be considered to be critical to the quality of the appraisal. In such instances the appraisal quality flag is left set to red, and the user is warned, on association of a value with the object, that the appraisal is highly suspect. The user may then elect to treat the appraisal skeptically.

If the missing elements are not considered critical, the appraisal quality flag is set to yellow at 120 and at 122 it is determined whether the missing data was significant. For example, it might be important, but not critical, in assessing the value of a piece of china such as a vase to know the date on which it was manufactured. In such case the appropriate appraisal quality flag would be set and the user informed. If at 122 it is determined that the missing elements provided were neither critical nor significant, the appraisal quality flag is reset to green at 124.

The description being as fully established as possible, the item is characterized at 125, an appropriate value data set is accessed at 126, and at 128 a value is associated with the item. Optionally, at 130 a report comprising the item value, the quality flag, and a complete description of the appraised item is issued.

Association at 128 of a value with the classified item can be accomplished in any satisfactory manner. A particularly simple and efficient means is to characterize the appraised item, according to its description, as a member of a class of items, and then to distinguish it in as much detail as possible from other members of its class, so that its value can be determined by comparison to one or more of a large set of similar and largely distinguishable items. The values of such items may be set out in one or more sets of tables, with each descriptive element and optionally the purpose of the appraisal, as previously described, being used to locate the closest possible match and its associated value. Suitable tables may be constructed through the appraisal and analysis of a number of items, with the larger number the number of items and distinguishing characteristics available for consideration and tabulation, the more particular and therefore more generally accurate the appraisal value available.

For example, as will be well understood by those of ordinary ability in the art, once they have been made familiar with this disclosure, it is possible to provide a complete table of values for diamond stones of given weight ranges, cuts, colors, and clarities, as of a given date; and, given such a table and appropriate descriptive information, to look up a value for a stone of a given description. The description may be made more detailed by adding additional values dependent upon stone source, age, and/or any number of other factors.

Another particularly efficient and useful alternative is to provide each basic aspect of the item being appraised a base value, using a series of factors determined by association with the remaining descriptive elements to either increase or decrease the base value, for example on a percentage basis, and then adding the factored values of the basic item aspects, and optionally applying further factors to the aggregated factored basic aspect values. For example, in evaluating an "emerald cut-step" diamond weighing 0.42 carats, a basic value per carat for a "pear shaped" stone is obtained from tables based on the color, clarity, and size of the stone, and this basic value is multiplied by the weight of the stone, in carats, and then by a factor, which can vary depending upon other factors such as size range or source, to adjust for the relatively unusual "emerald cut-step" shape. The value of a mounting ring can be appraised in the same manner, with the value of the complete ring determined by adding the stone and ring values together, and optionally applying further factors based on, for example, workmanship or manufacture.

In determining values based on tables, it is also frequently useful, in addition or as an alternative to simple look-up methods, to use interpolation or extrapolation techniques, many suitable methods of which are well known, as a generally preferred alternative to rounding to the nearest tabulated value. Such techniques can be used alone to determine item values or used in combination with other methods. For example, values of stone per unit weight are conveniently tabulated in steps such as, for example, tenths or hundredths of carats. When a weight falling between two tabulated values, or outside a tabulated range is reported, a value which is acceptable for most purposes may be obtained by linear or non-linear interpolation or extrapolation, respectively.

Reports issued with appraisal values may of course be tailored to the purpose of the appraisal. Suitable variations in addition to those described herein will occur immediately to those of ordinary skill in the art.

FIG. 1 may also be used to Illustrate the automatic updating of an appraisal, as this generally reduces to the case in which a complete description is entered at 102 and analysis proceeds directly from 102 through 104 and 106 to 124 and on. In such cases the process may be initiated automatically, as for example at a predetermined date and/or time, or on a predetermined periodic basis, or may require some user intervention, as for example a response to a prompt displayed on a user interface screen.

Preferably, process and method aspects of the invention are implemented on digital computers or other data processing equipment for efficient use. In such embodiments the data processing equipment is adapted by means of software, hardware, or other enabling means to carry out the steps and process and store data as described above. The processes can be enabled either as a stand-alone unit on a single machine, or by groups of machines connected by networks such as the Internet or dedicated, secure local-area networks. In networked implementations software may reside either on one or more remote terminals or on one or more central host servers. It has generally been found to be preferable, however, in network installations to retain data sets on a central server, to ensure uniformity, in analysis and proper maintenance and updating of appraisal data. Secure connections and data protection are preferred.

Figure 2:
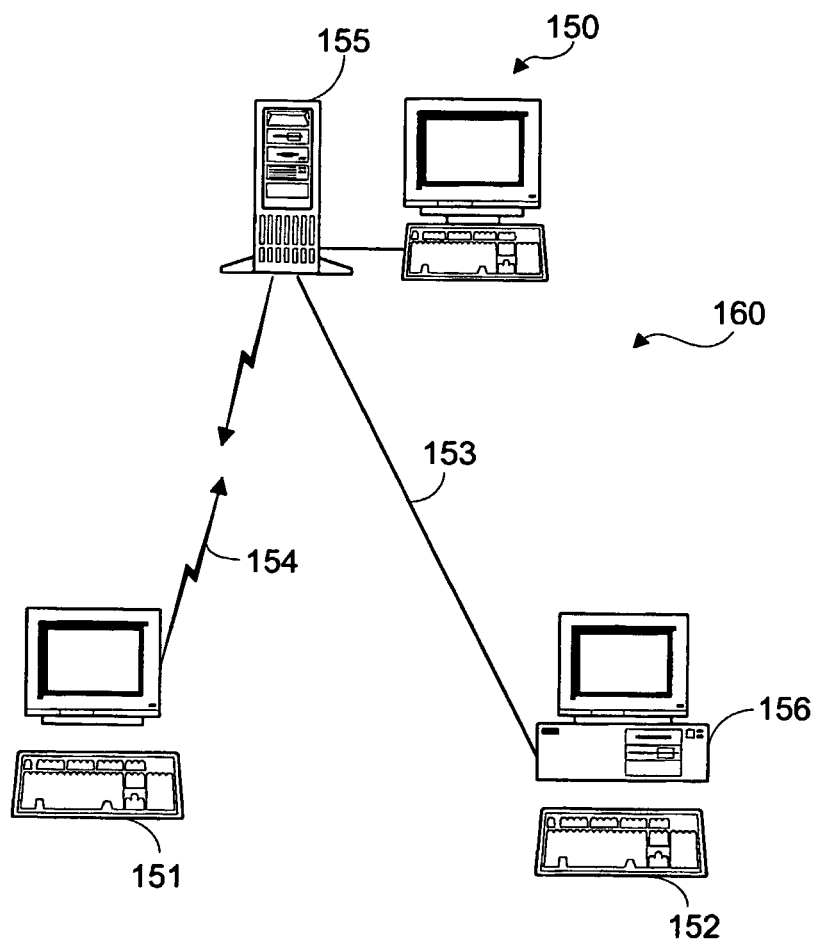
FIG. 2 is a schematic diagram of a data processing system adapted for valuing jewelry and other items according to the invention.

FIG. 2 is a schematic diagram of a data processing system adapted for appraisal of jewelry and other valuable items according to the invention. System 160 comprises server or host 150, which comprises one or more data storage device(s) 155, and optional remote terminals 151 and 152. Data storage devices may be permanent (as for example permanent storage electromagnetic disk drives or compact disks) or temporary (as for example volatile electromagnetic memory). Remote terminals 151 and 152 are connected either by dedicated connection 153 or by indirect means 154, such as a telecommunications or cable network, or wireless arrangement. Any suitable connection will serve. In a preferred embodiment a single host or server 150 serves a plurality of remote terminals 151, 152, via a variety of connections. Data sets comprising data for provision of default values for missing description elements and value data for described items reside on data storage device 155. In the embodiment shown, the use of a plurality of remote user terminals 151, 152, facilitates gathering of description and assessment data from an increased number of user sources.

EXAMPLE

FIGS. 3-16 illustrate user interface screens for a preferred embodiment of an implementation on a data processing system of a preferred process according to the invention. The Figures consist of screen-shots of various user interface screens presented by the data processing system to the user for interactive entry of descriptive elements and for selection and control of the type appraisal process to be performed. Input of optional related data is also facilitated. The screens are produced by a test version of the JEMS ("Jewelry Expert Multiapp System) computer software produced by JCRS of Oakland, Calif., and are subject to copyright. The screens shown by the Figures are meant to be exemplary only; the program is still under development and in any case represents only an example of one implementation of the invention disclosed herein.

The program used to produce the user interface screens of FIGS. 3-16 is written in the "Windows" programming format. User data entry is accomplished by any suitable method, including conventional keyboards and other interface controllers such as mice, trackballs, and pointers. Data is optionally either typed into provided fields or selected from system-provided values through the use of "pull-down" menus such as are in common use in Window-style programs. To enter data by typing, a cursor is located within a data field presented on the screen. Activation of, for example, a mouse button locks the cursor in position and the data may be typed directly into the field. When a given entry is complete use of the "Enter" key or selection of an other data entry field of other item causes the data entry to be sent to the host computer for further processing. To enter data by use of a pull down menu, an arrow icon such as that shown in field 226 of FIG. 4 is selected. This results in presentation of a list of items or options such as that shown at item 272 in FIG. 10b. The desired choice is made by using up or down arrows, or other suitable keys, from a keyboard, or through cursor placement and selection using a mouse.

JEMS software is produced primarily for insurance underwriting and claims processing tasks, and is appropriate for use both for insurance under homeowner's policies or as separate coverage, as for example under separate inland Marine agreements. It provides record keeping capabilities for descriptive content and valuation of valuable personal property. Valuation of appraised items is provided through collection of pricing data and the provision of default values in accordance with the disclosure herein. JEMS is compatible with other software products and complies with ACORD (Agency Company Organization for Research and Development) AL3 standards.

Figure 3:
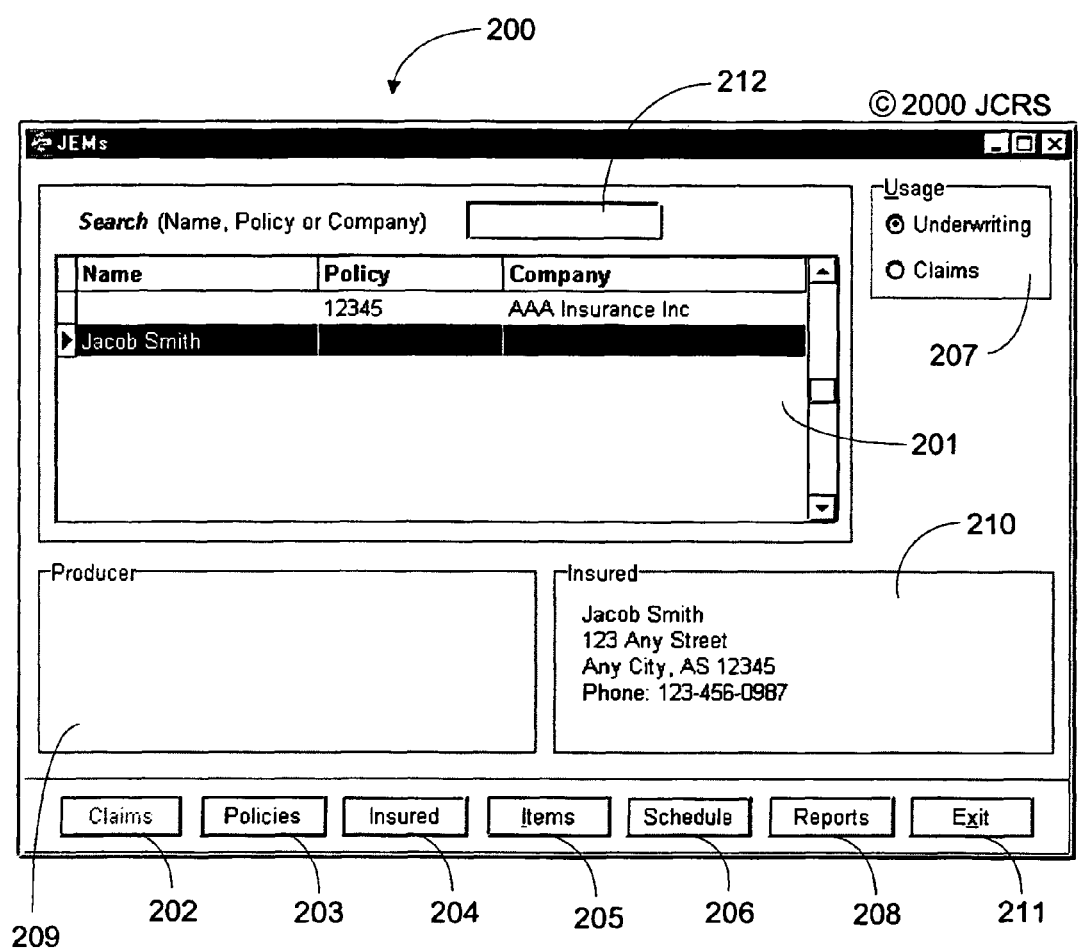
Figure 4:
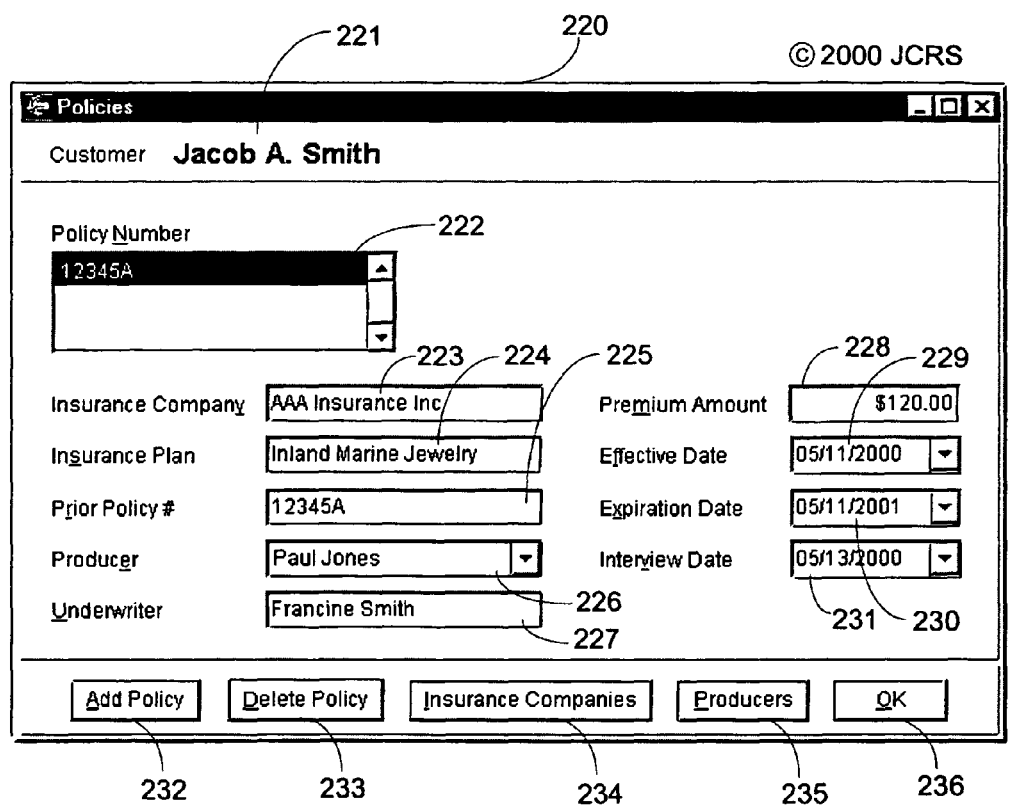

JEMS base screen 200 shown in FIG. 3 facilitates selection and control of appraisal methods and purposes, and basic selection and identification of property owner and insurer information; and facilitates basic control of the appraisal process. Field 201 provides a list of distinct previously-entered appraisal tasks (only one is shown in this Example). The list in field 201 is searchable or sortable by name, policy, or company, by entering a search request at field 212 or by selecting any one of the labeled column headers "Name," "Policy," or "Company." Any one of the previously-entered appraisals may be accessed for further analysis. Alternatively, a new analysis may be started by selecting the purpose of the appraisal by making the appropriate selection at field 207 and then working generally left to right through the menus presented by selection of options at the bottom of the screen, including options 202, 203, 204, 205, 206, and 208.

To assist in guiding the user through the appraisal process and eliciting the greatest possible mount of information in the most expeditious and efficient possible manner, various options are enabled or disabled during various portions of the process. For example, because "underwriting" has been selected as the analysis type at 207, option 202, "Claims" is disabled in the view shown. Selection of an option or an attempted data input before sufficient supporting data has been entered results in presentation of a warning screen and a request and guidance for entry of the required information, or optionally in a plain refusal of th machine to accept the information.

Throughout the Figures those options and data entry fields which have been enabled are shown in dark relief, while non-enabled options and fields are shown in relatively light relief. Compare for example "claims" option 202 and "policies" option 203 in FIG. 3.

Fields 209 and 210 display, If such exists, previously-entered data related to the current selection in Field 201.

To complete an appraisal of a piece of jewelry suitable for underwriting use, option 203 "Policies" is selected. This results in presentation of screen 220 of FIG. 4, in which the user is enabled to enter data related to a particular insurance policy, or to select a previously-entered policy at field 222. Policies may be drawn to one or several items of jewelry or other personal property. Policy information includes customer name 221; policy number 222; insurance company 223; insurance plan title 224; related policy number 225; producer identity 226; underwriter identity 227; premium amount 228; effective date 229; expiration date 230; and interview date 231. Any of items 223-231 may optionally be provided a list of previously-entered default values, for example by means of pull down menus. A pull down menu may be generated by selecting any of the down-arrow items shown in fields 226, 229, 230, or 231, as described herein. Additional policies or producer, or company identities may be created, or policies deleted, by selection of options 232, 233, 234, or 235, as appropriate, and entry of suitable information.

Figure 5:
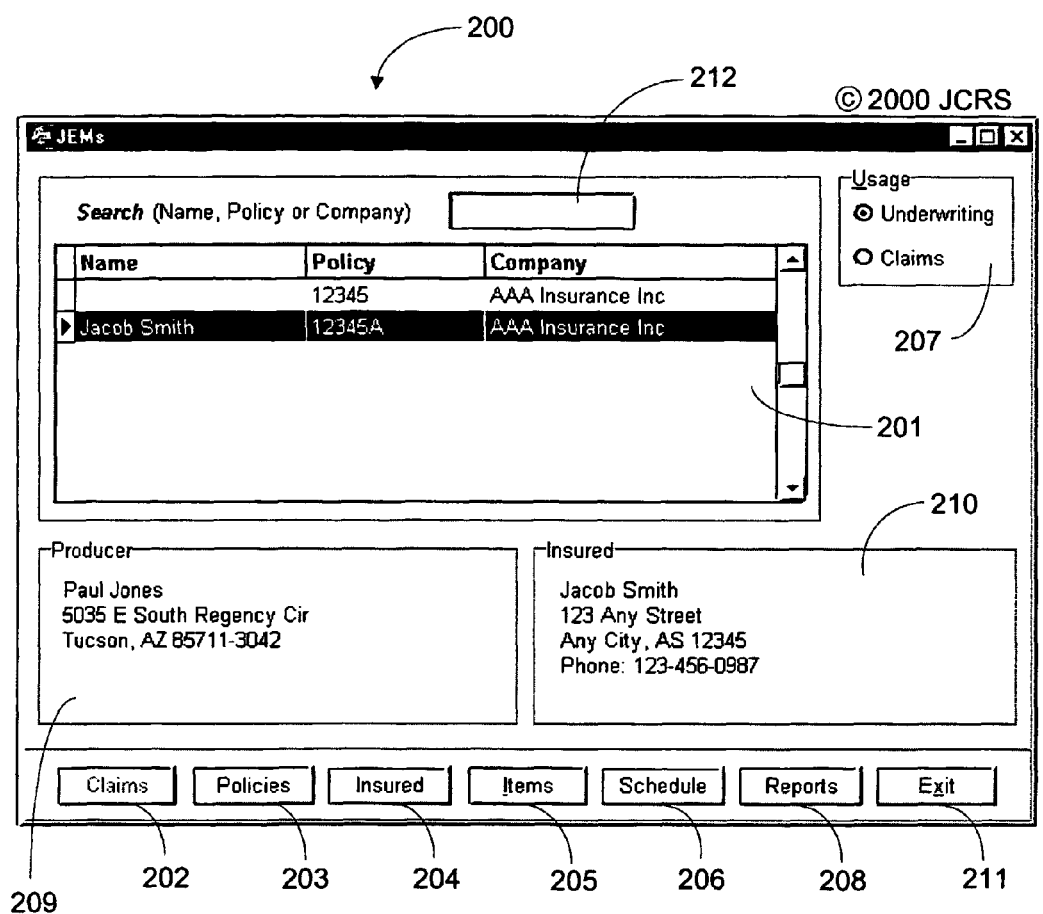
Figure 6:
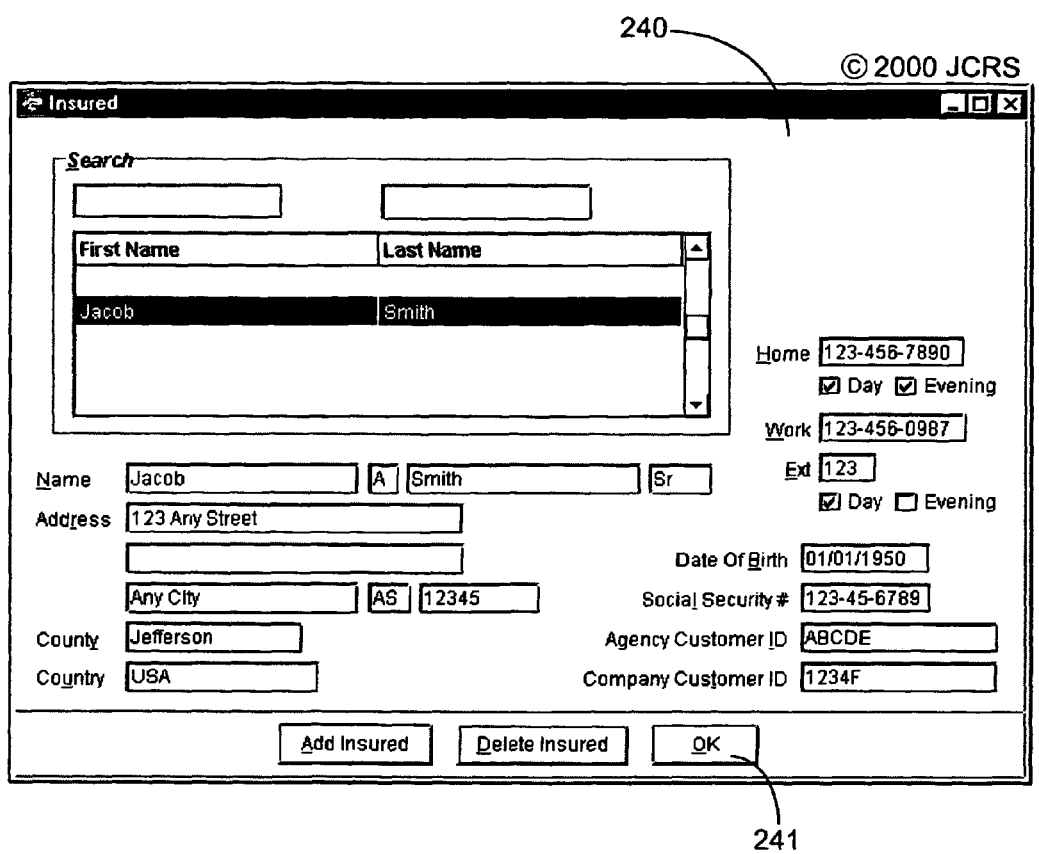

Entry of data and selection of suitable options in fields 223-231 and selection of item 236 signifies completion of data entry/selection and returns the user to screen 200 of FIG. 3, which, as shown in FIG. 5, now reflects the entry of additional information. Selection of option 204 "Insured" from FIG. 5 results in presentation of screen 240 of FIG. 6, in which information related to the insured party may be entered. As for all portions of the JEMS program, information may be entered. Data may be entered in the fields of FIG. 6, and throughout the other JEMS screens shown in the Figures, in any suitable conventional fashion, by use of a keyboard, pointing device such as a mouse or trackball, or other input device. Upon completion of entry of information related to the insured, selection of option 241 causes a return to screen 200.

Figure 7:
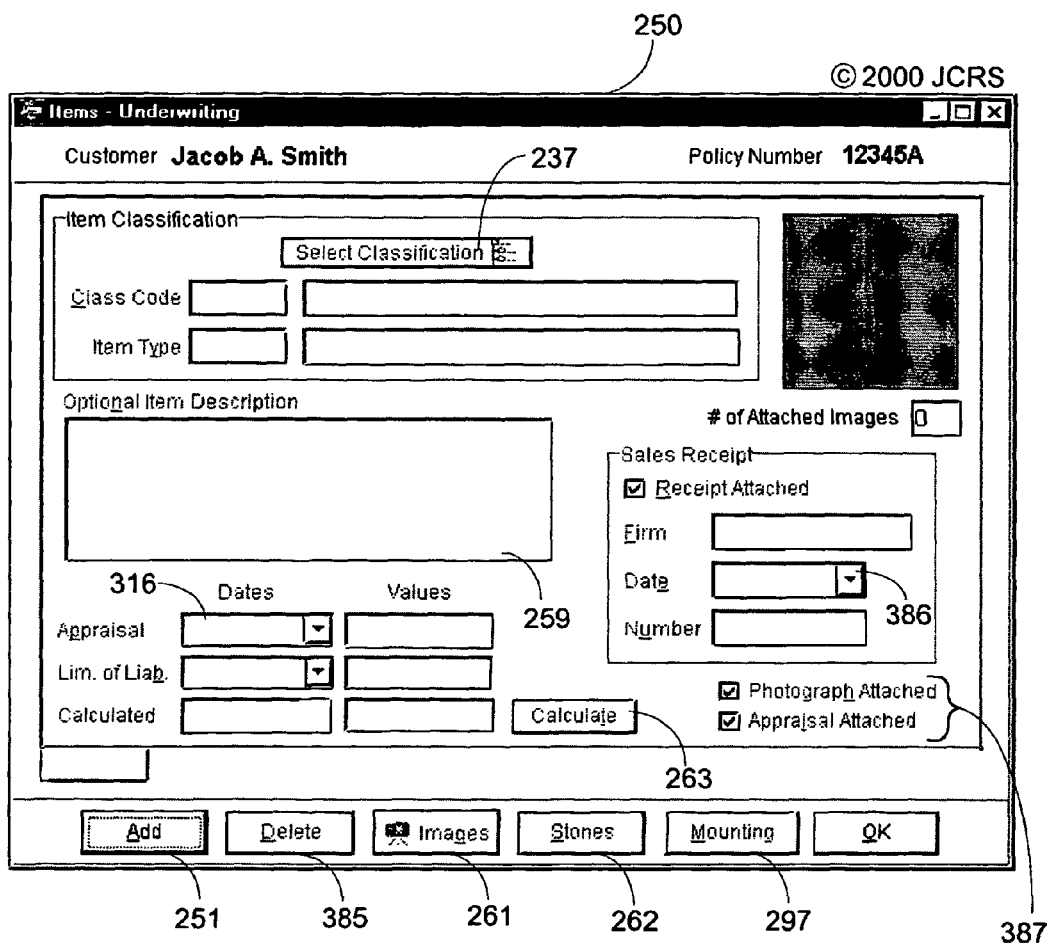

Selection of option 205, "Items," in FIGS. 3 and 5 results in presentation of an "Items" screen as shown in FIG. 7. Items screen 250 is adapted to elicit a description of an item of property such as a piece of jewelry. That is, it guides the user through the process of characterizing the item for provision of lacking data and completion of the appraisal process. The process of identifying or describing an item new to the system begins with selection of option 251 "Add" and thereafter of item 237 "Select Classification." As shown in FIG. 7, for a new appraisal item 237 is enabled only after selection of option 251

Figure 8A:
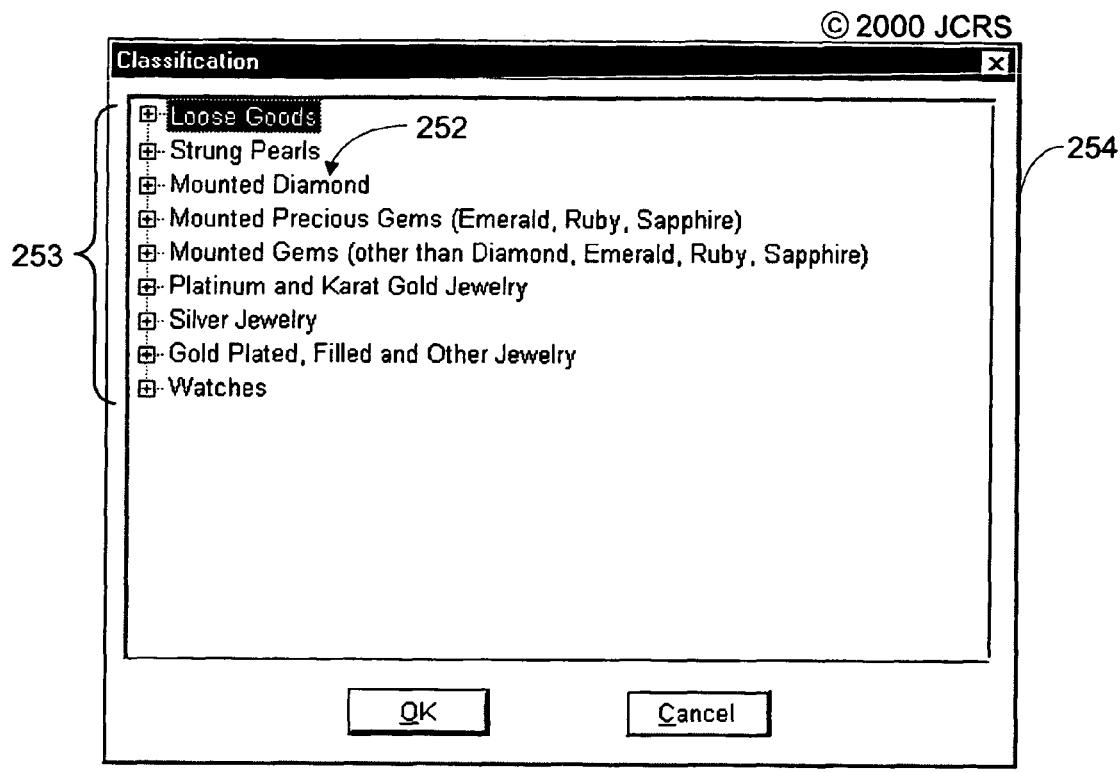
Figure 8B:
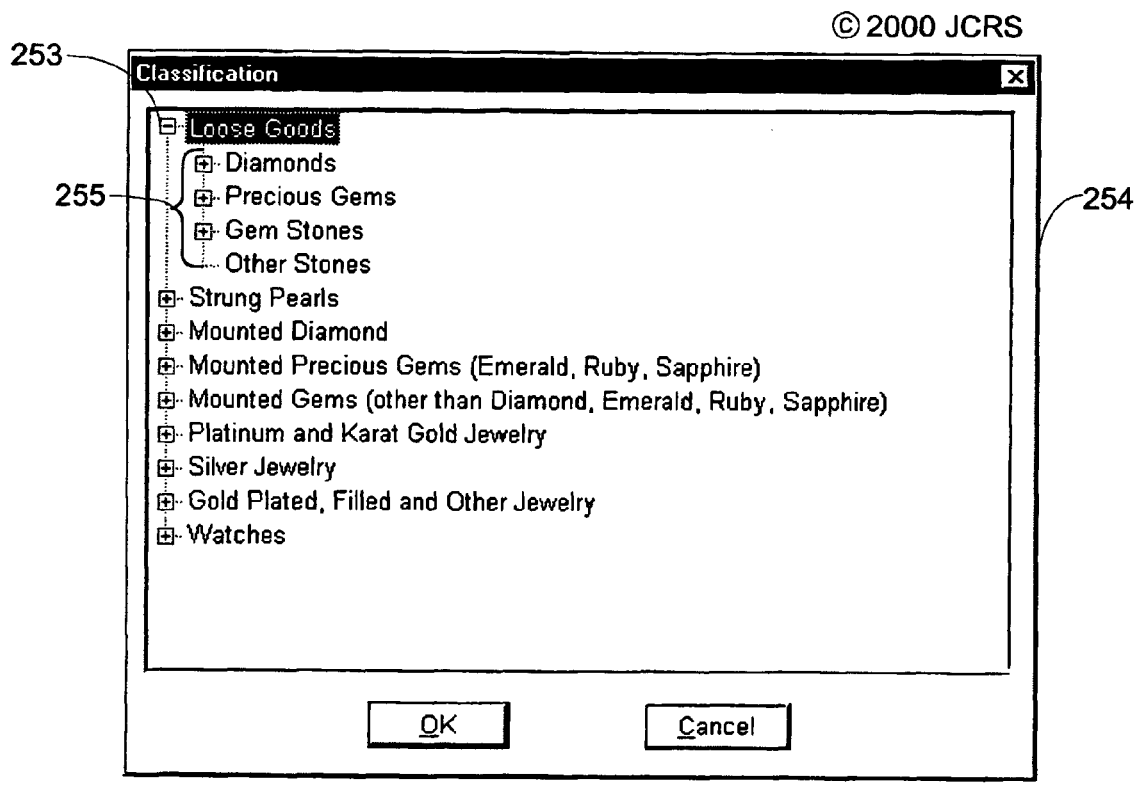
Figure 8C:
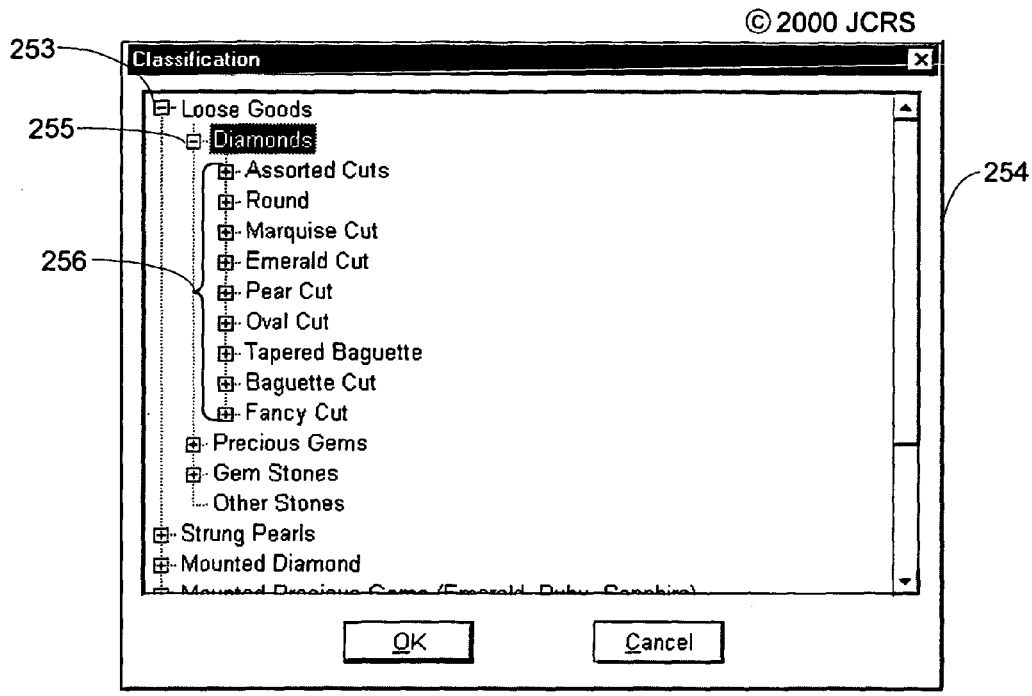
Figure 8D:
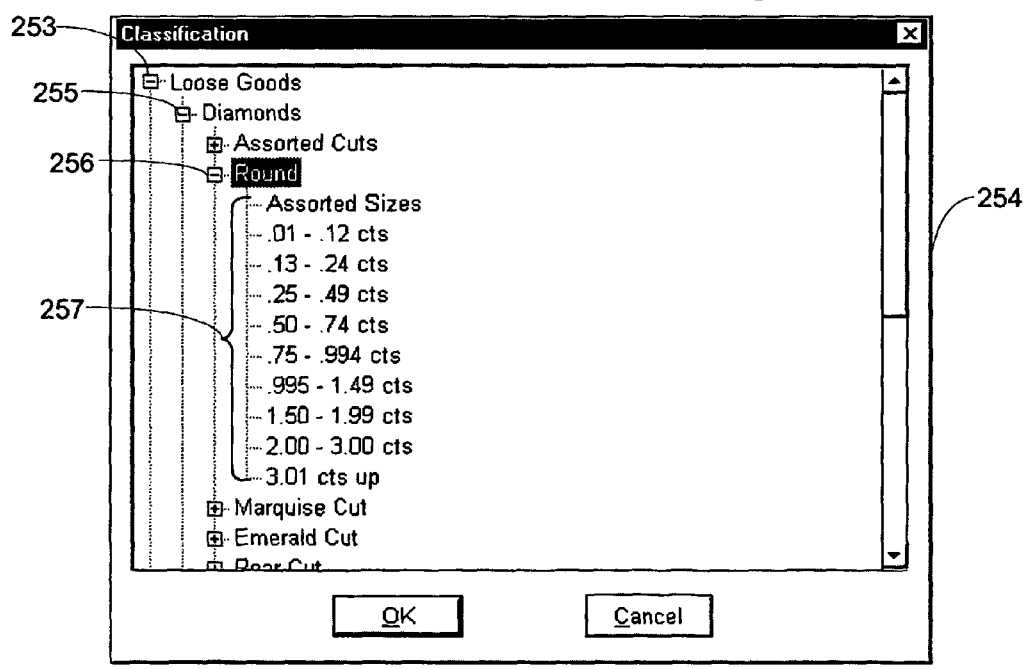

Selection of item 237 enables a list or menu 252 of primary personal property classifications 253 as shown in menu screen 254 of FIG. 8a. Selection of a primary classification 253 in list 252 enables a list of secondary level classifications 255, e.g., stone types, as shown in FIG. 8b; selection of one of the secondary level classifications 255 optionally enables a tertiary list 256, e.g., cuts, as shown in FIG. 8c, and so on, until a level of distinction which will enable a desired level of characterization and accuracy in the appraisal has been enabled. In FIG. 8d a representative fourth-level distinction list 257, stone weight, is shown.

Figure 8E:
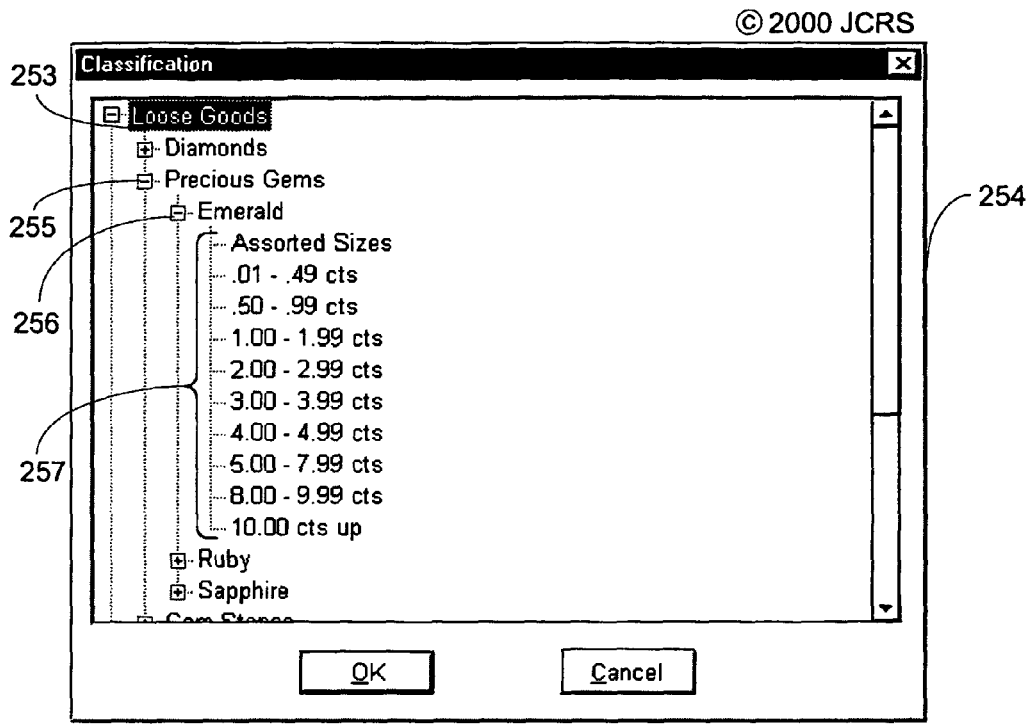
Figure 8F:
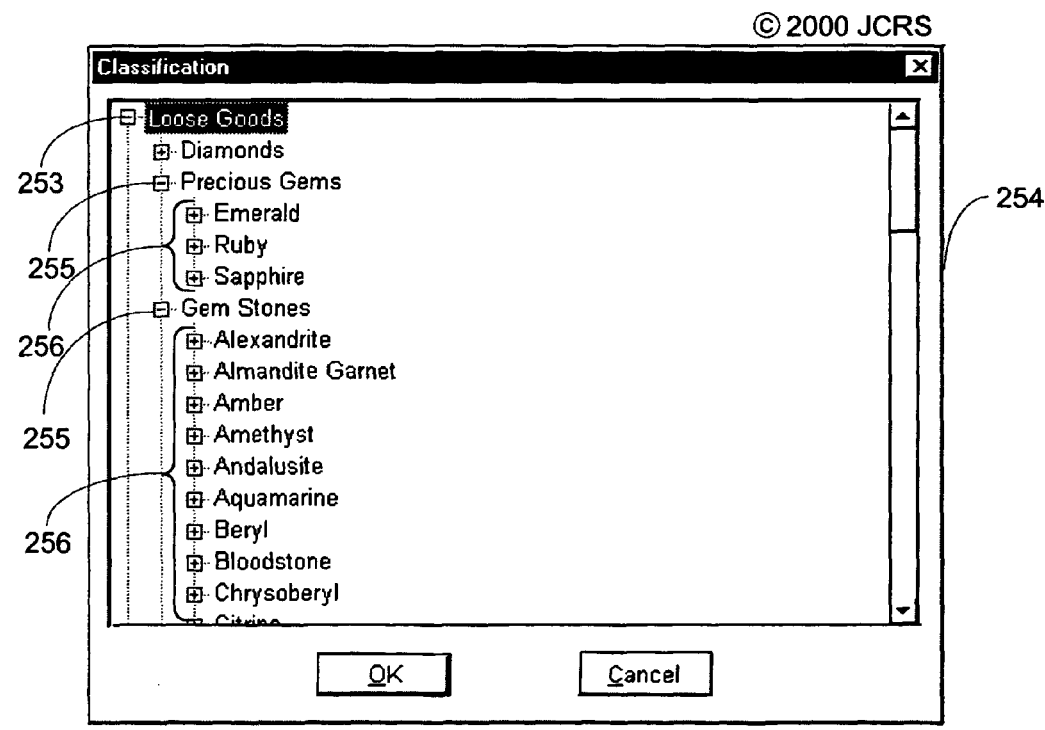
Figure 8G:
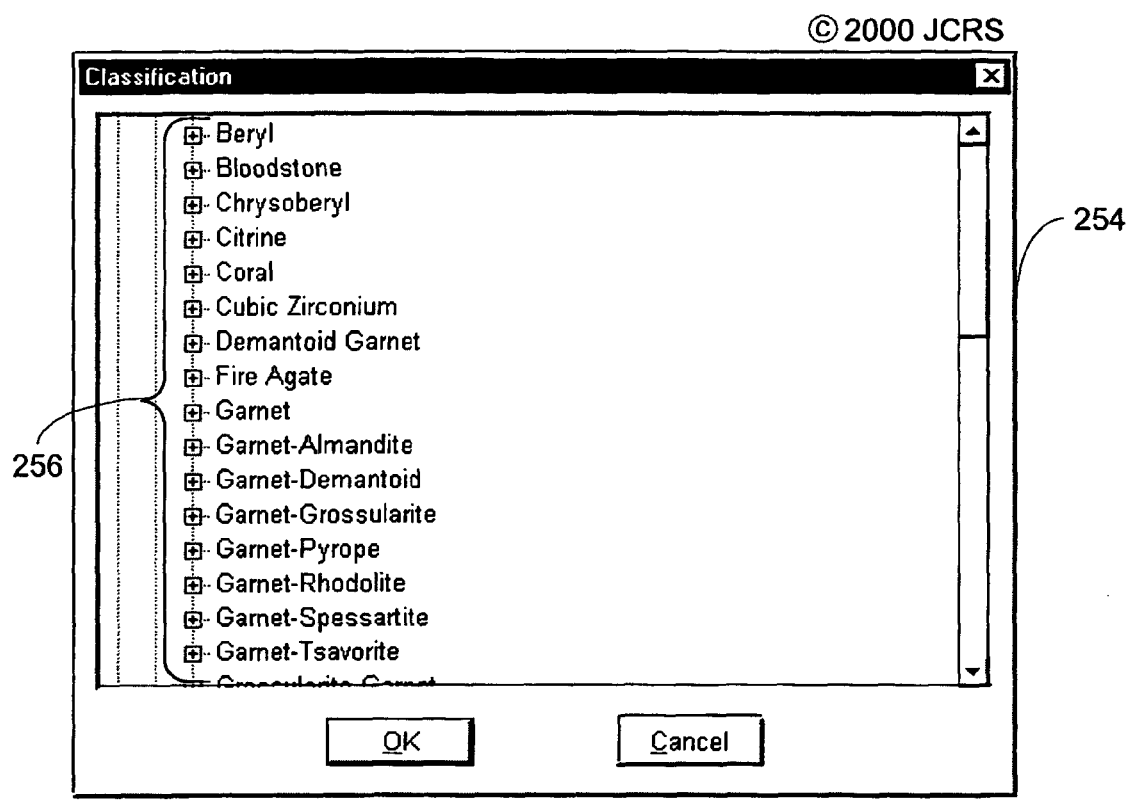
Figure 8H:
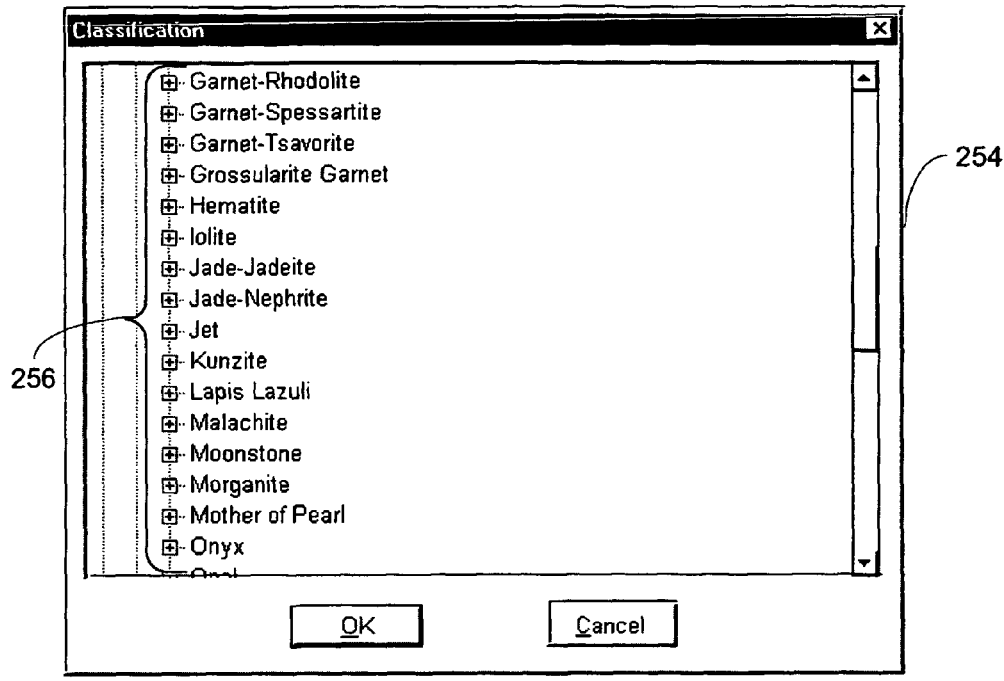
Figure 8I:
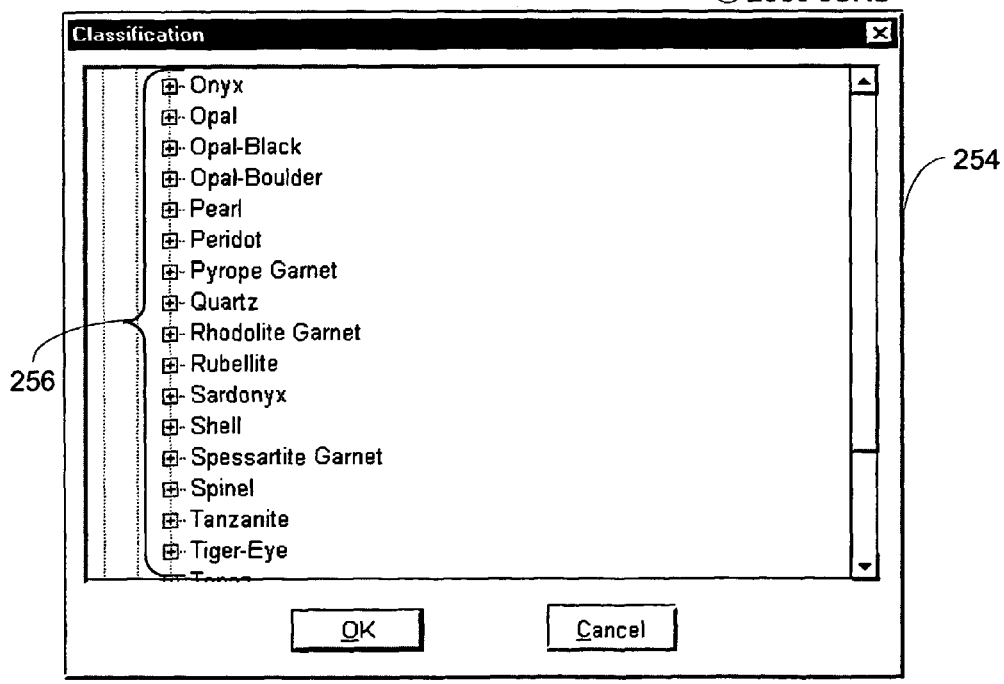
Figure 8J:
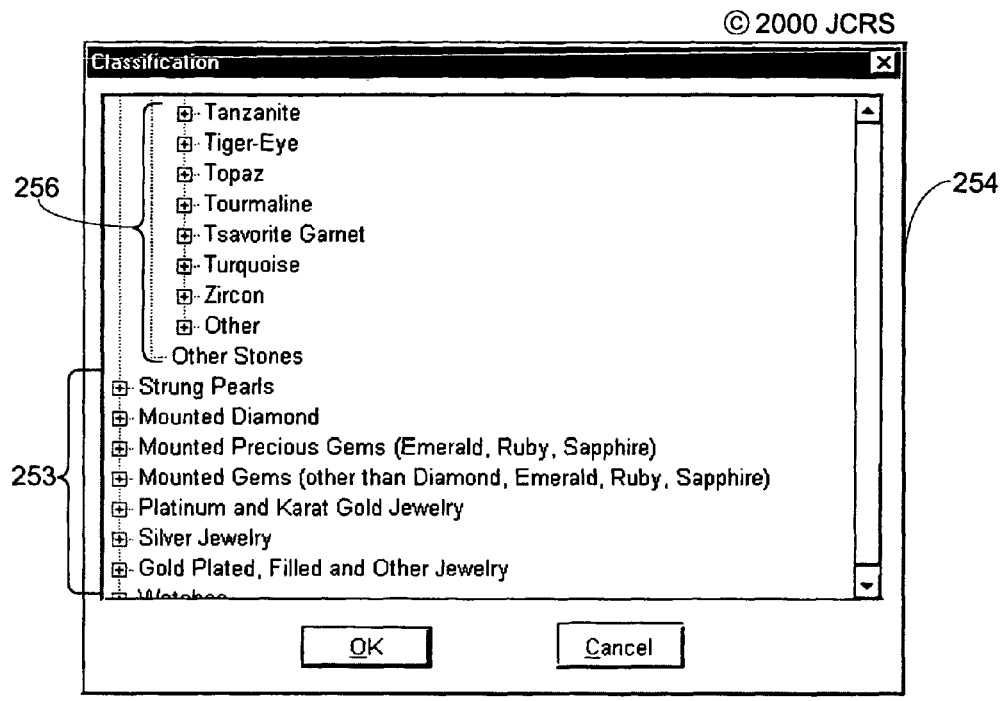
Figure 8K:
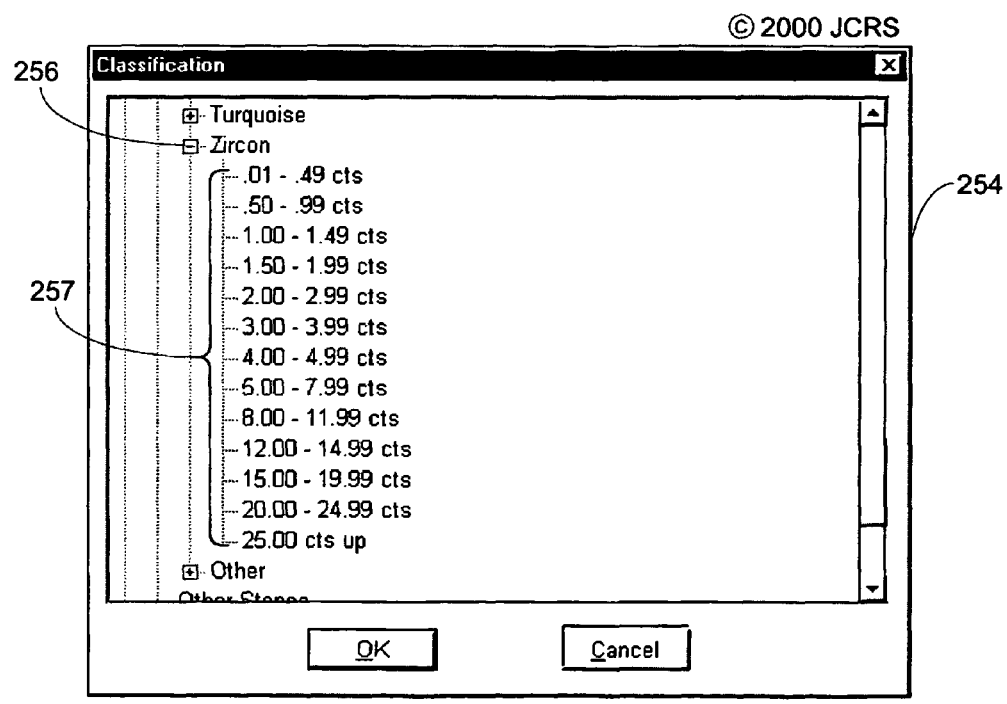
Figure 8L:
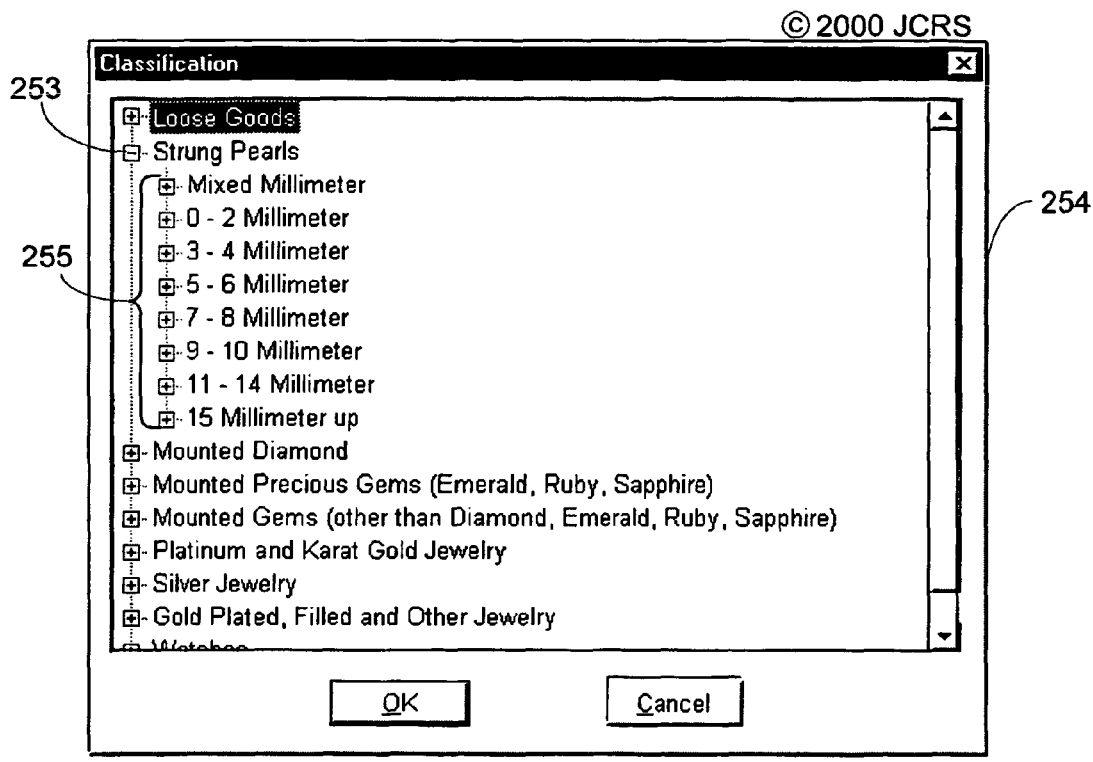
Figure 8M:
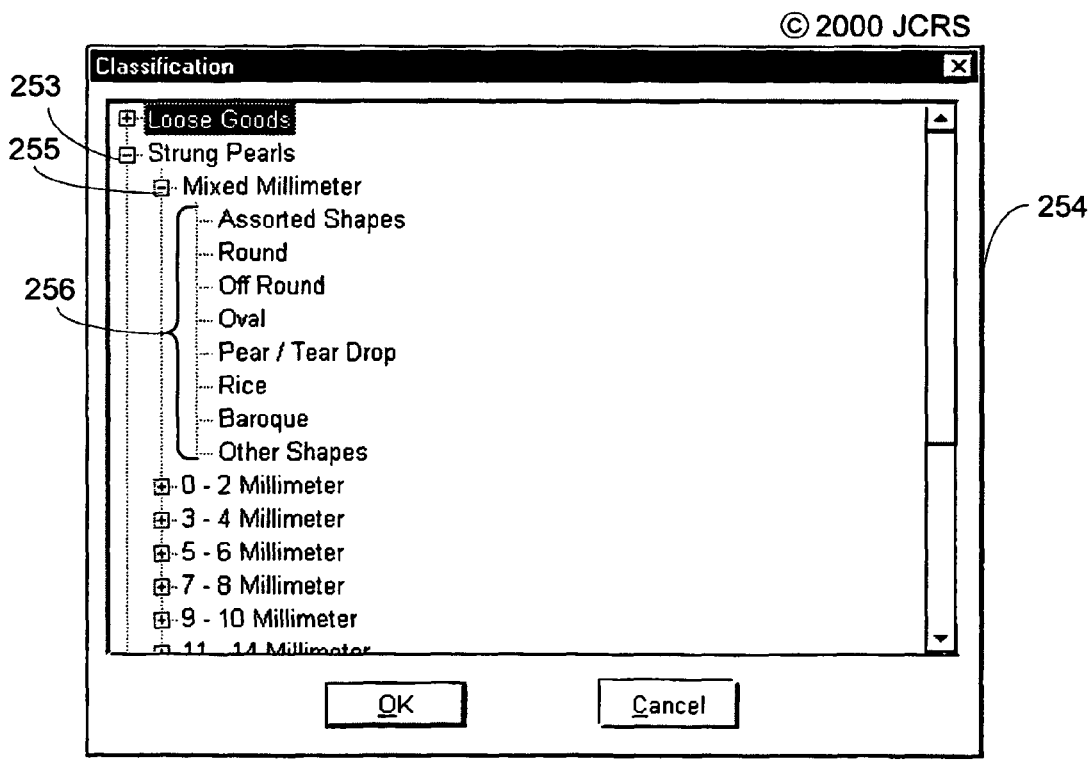
Figure 8N:
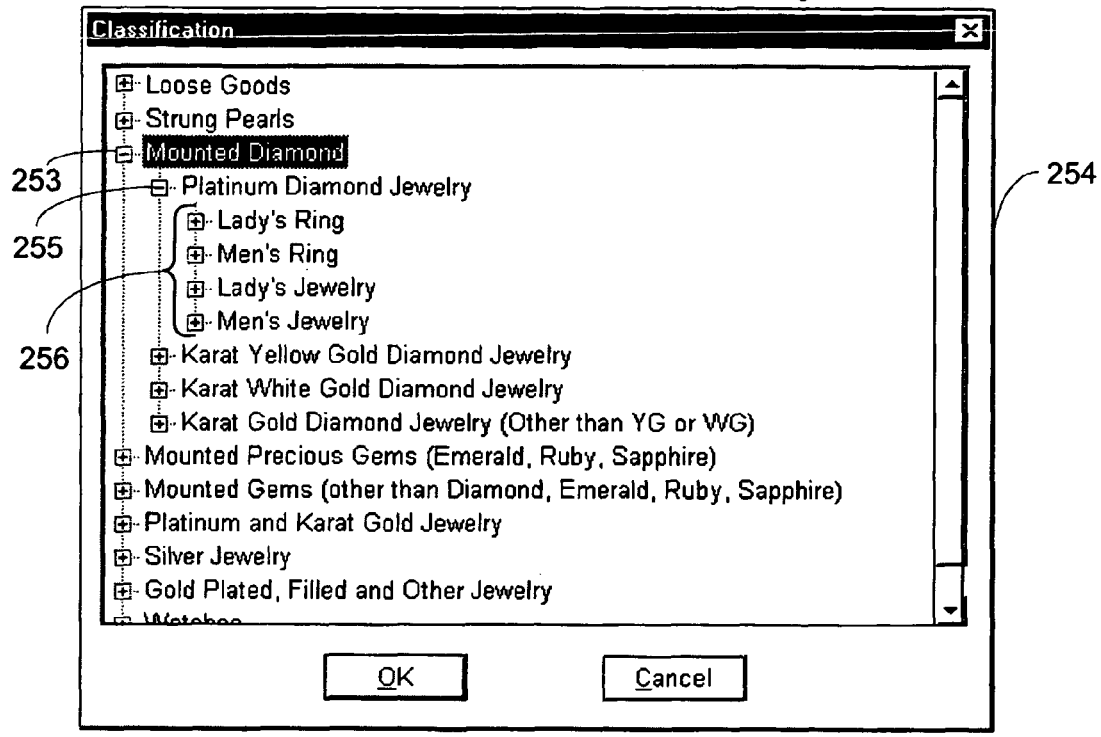
Figure 8P:
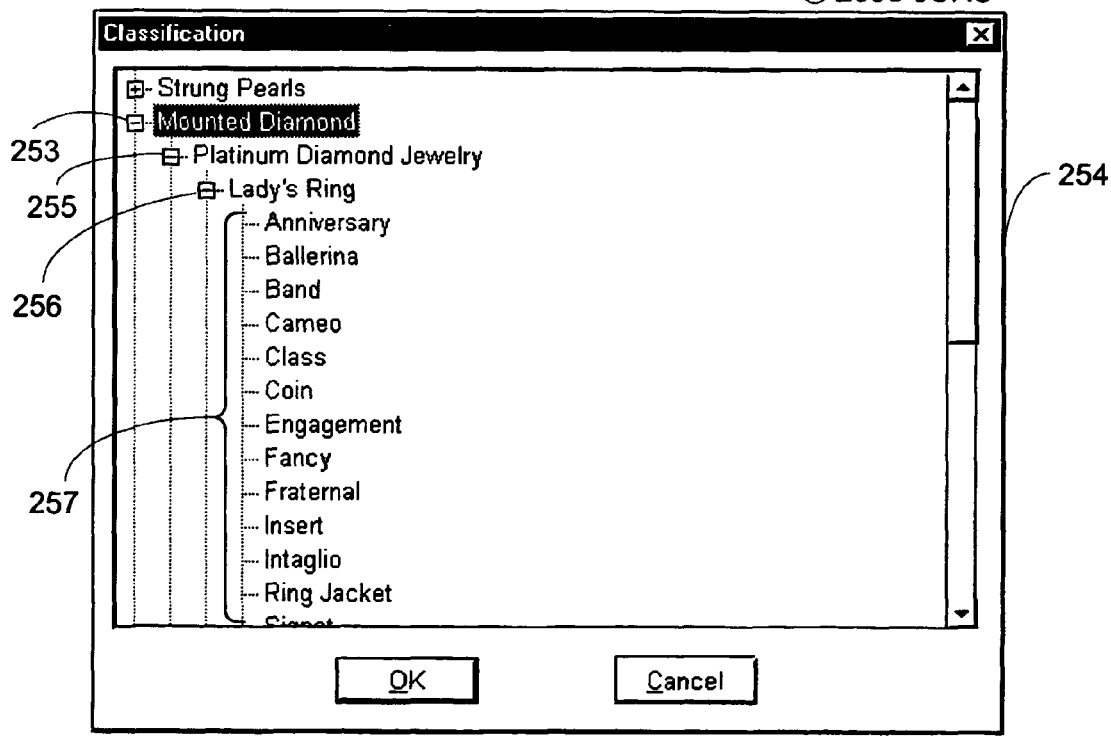
Figure 8Q:
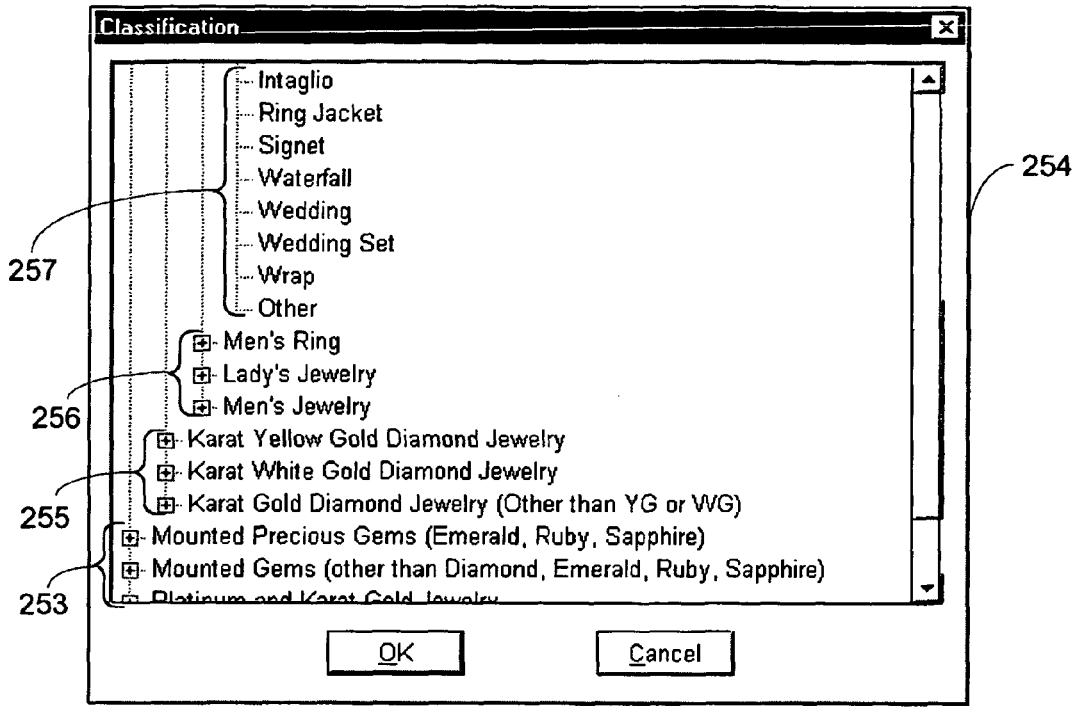
Figure 8R:
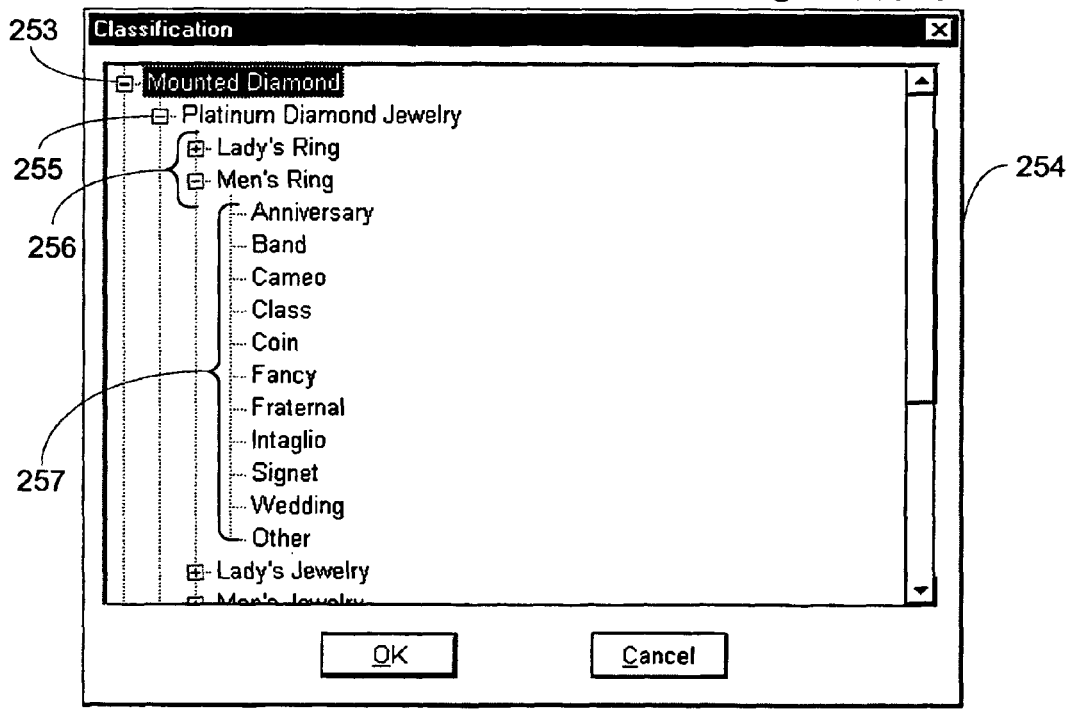
Figure 8S:
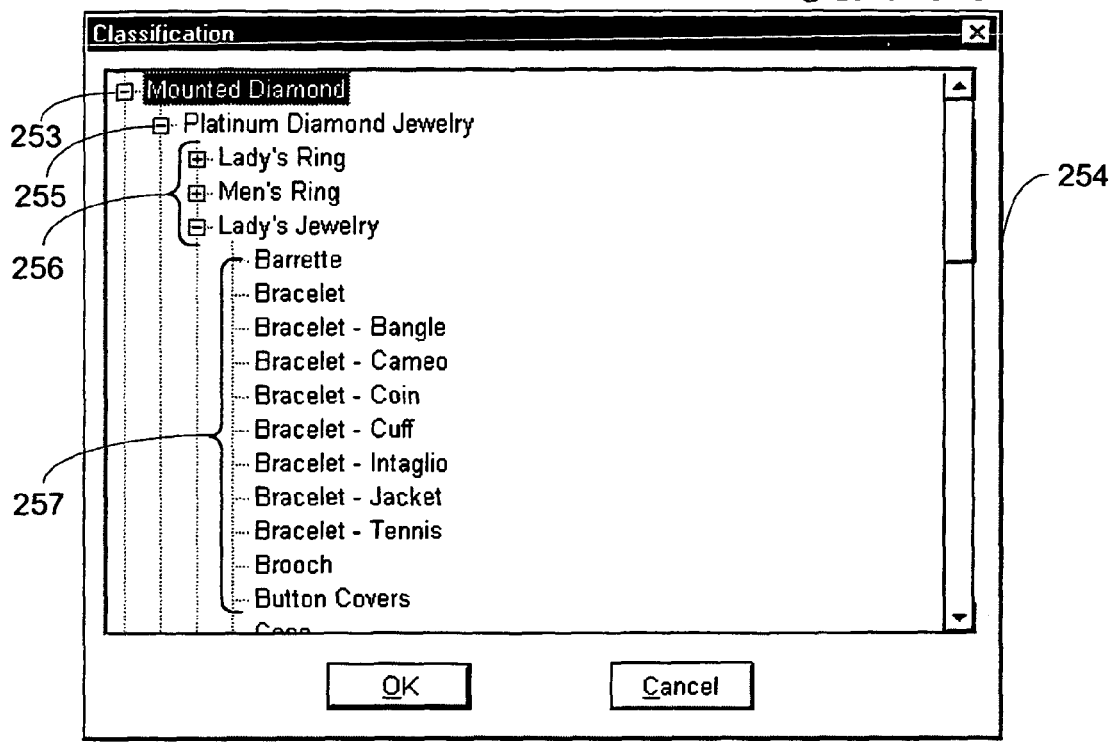
Figure 8T:
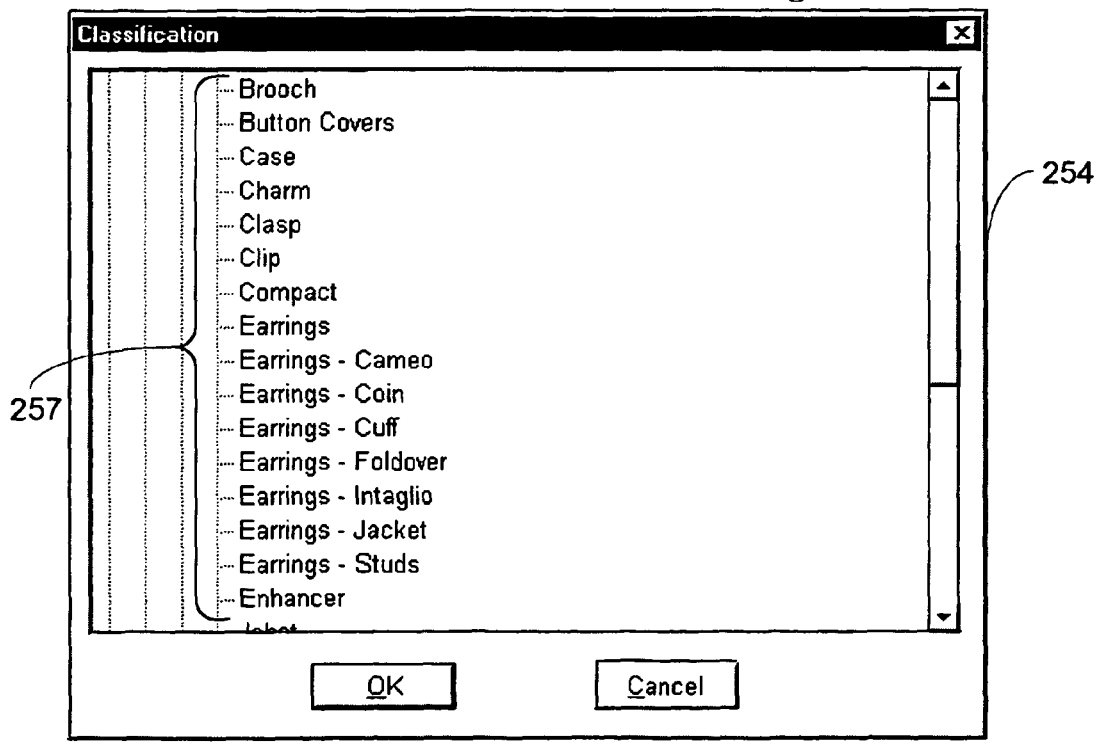
Figure 8U:
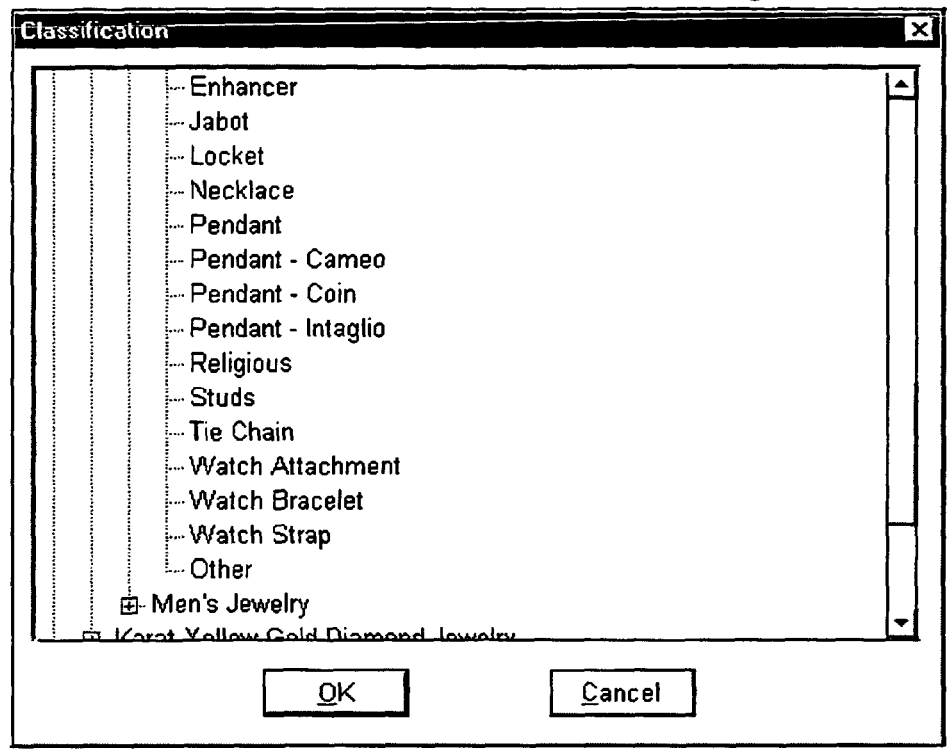
Figure 8V:
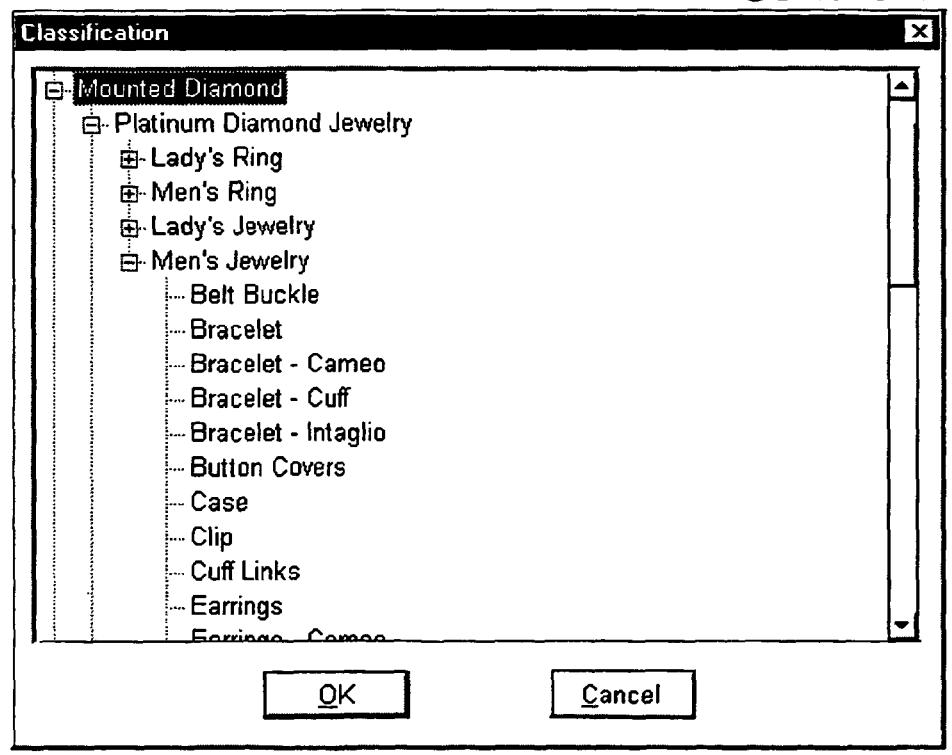
Figure 8W:
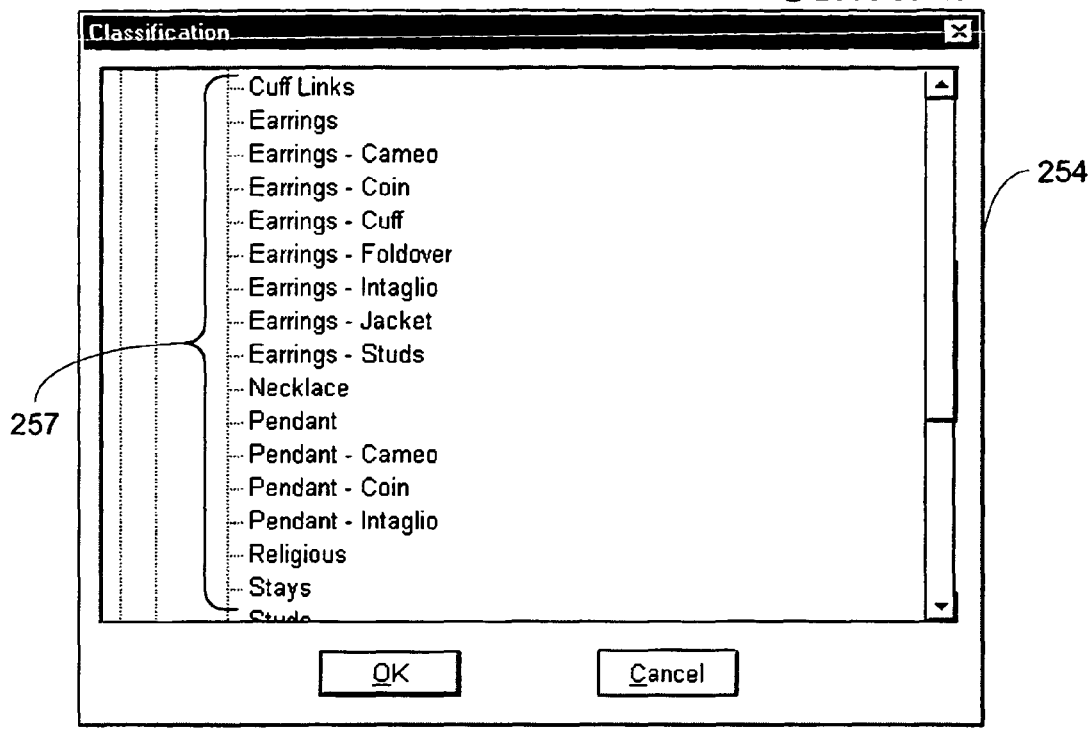
Figure 8X:
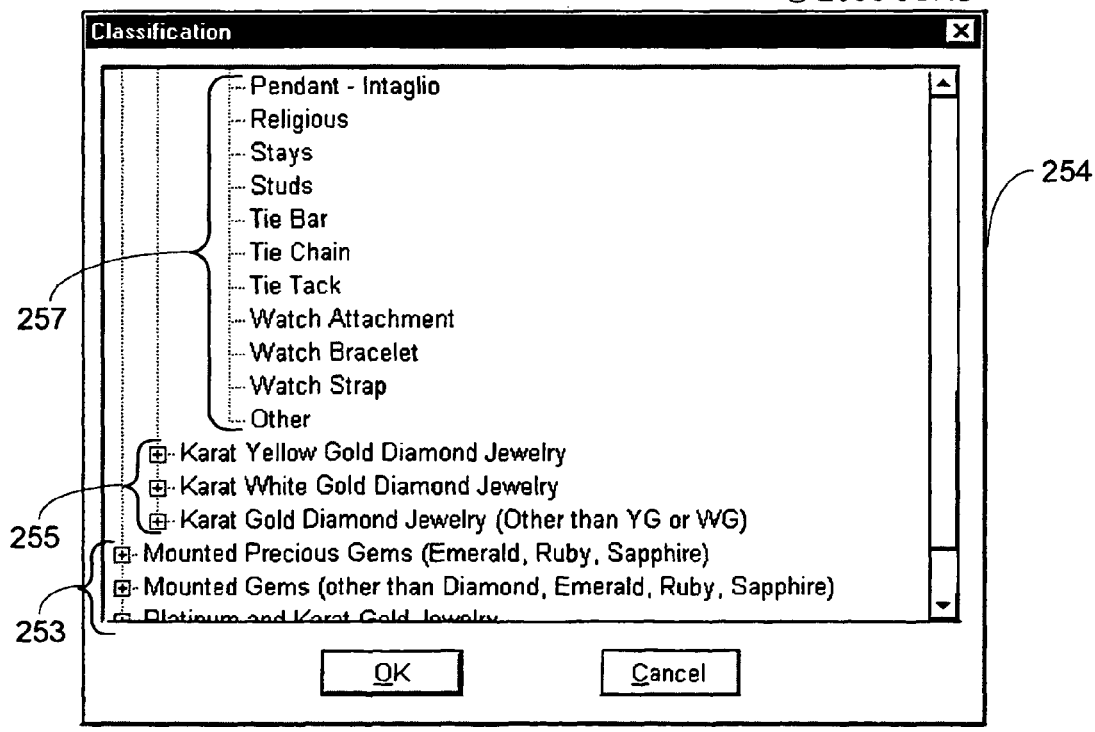
Figure 8Y:
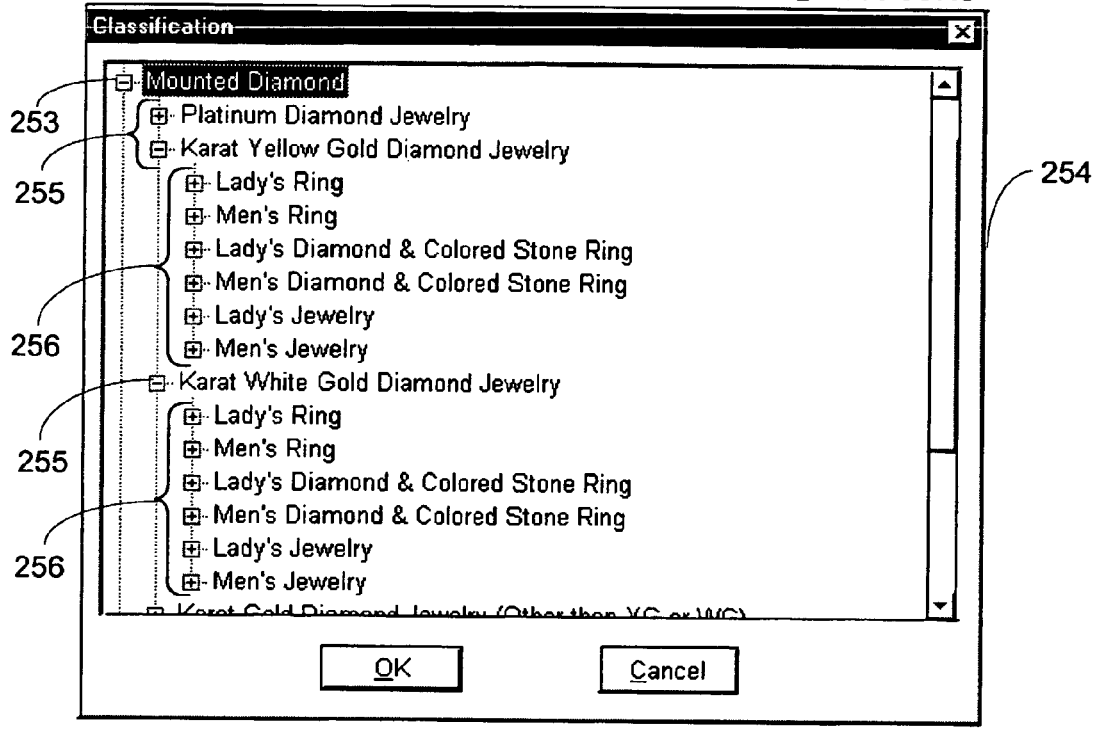
Figure 8Z:
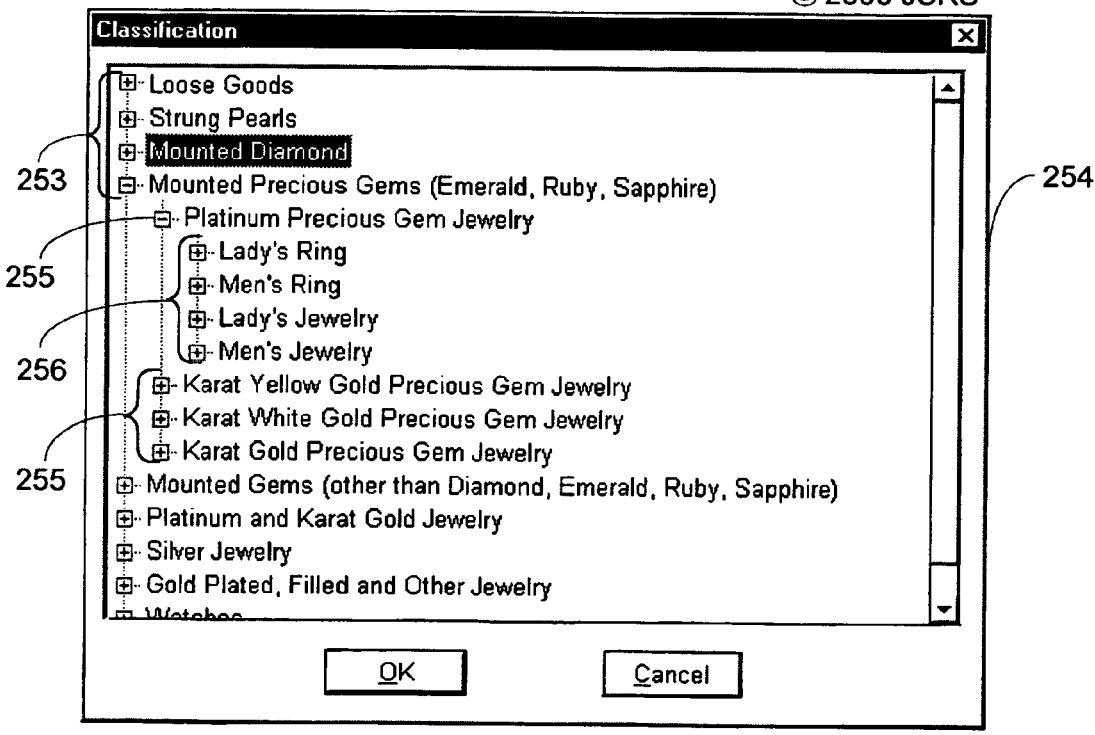
Figure 8A:
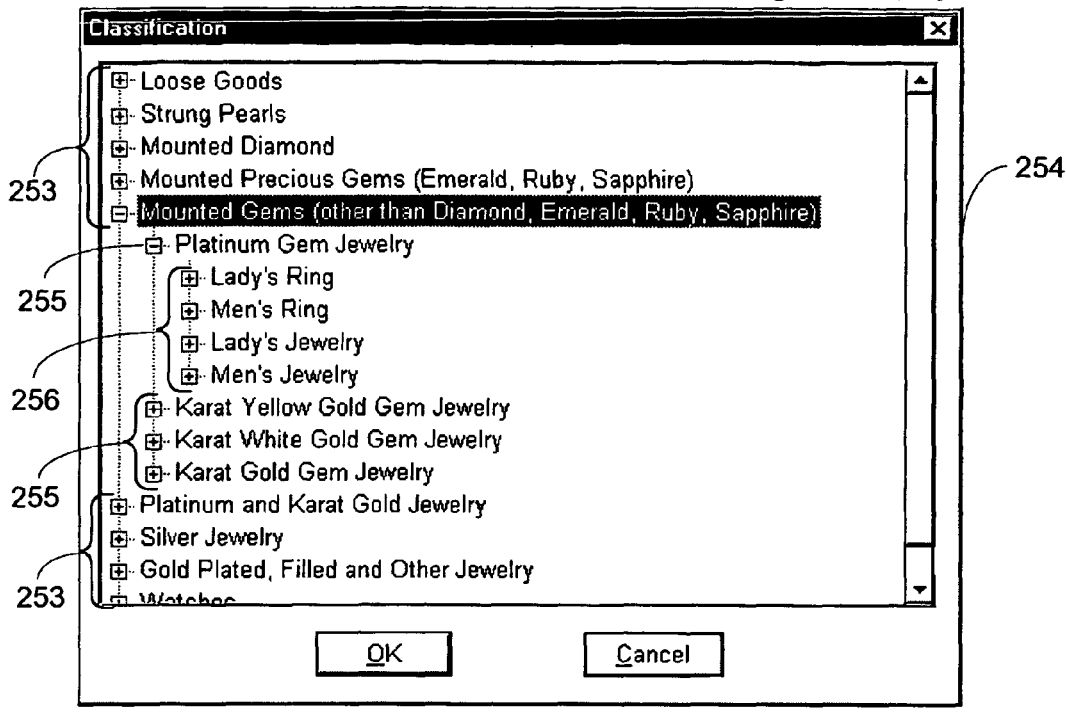
Figure 8B:
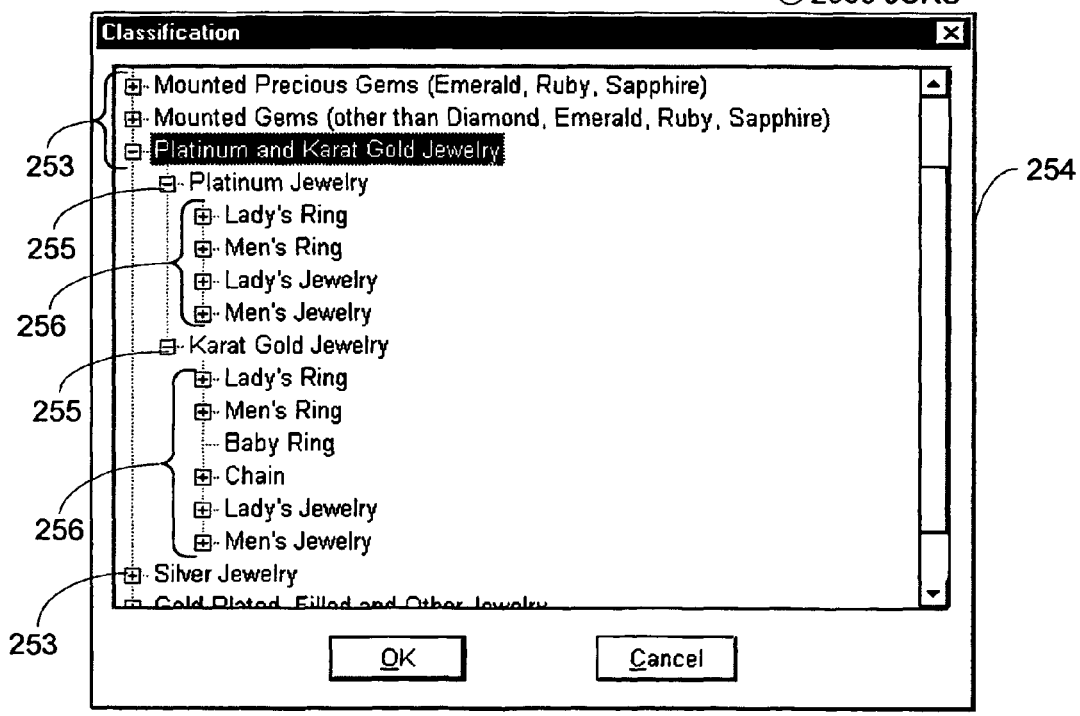
Figure 8C:
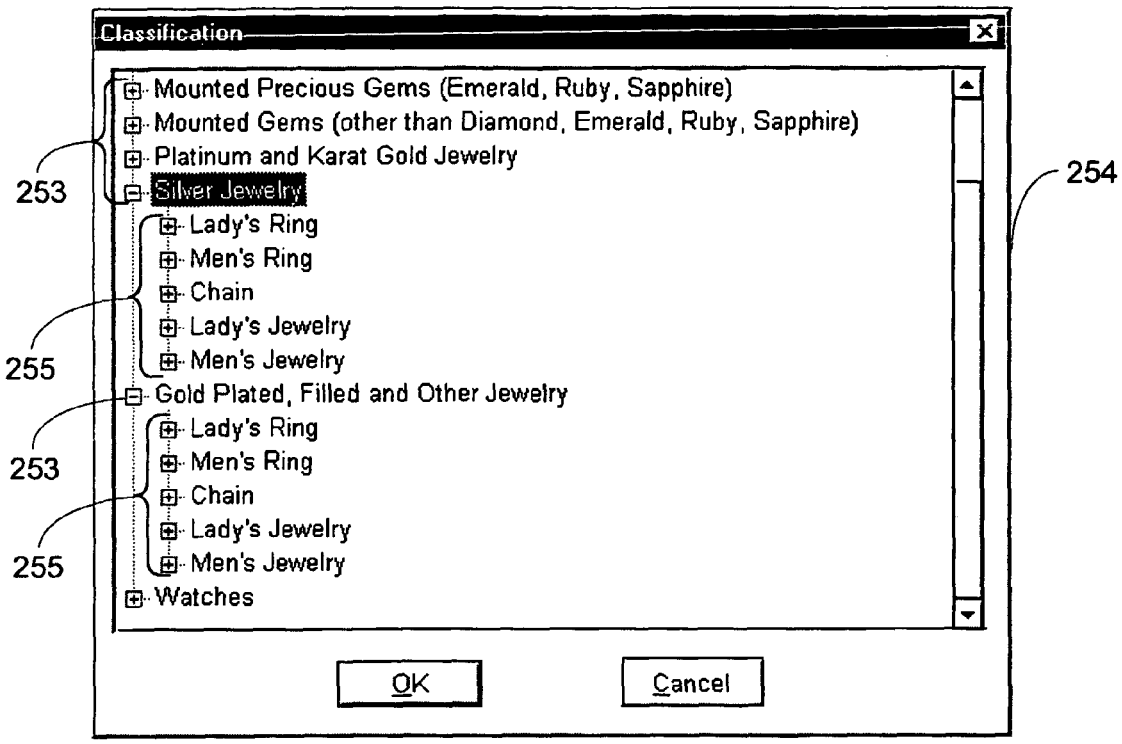
Figure 8D:
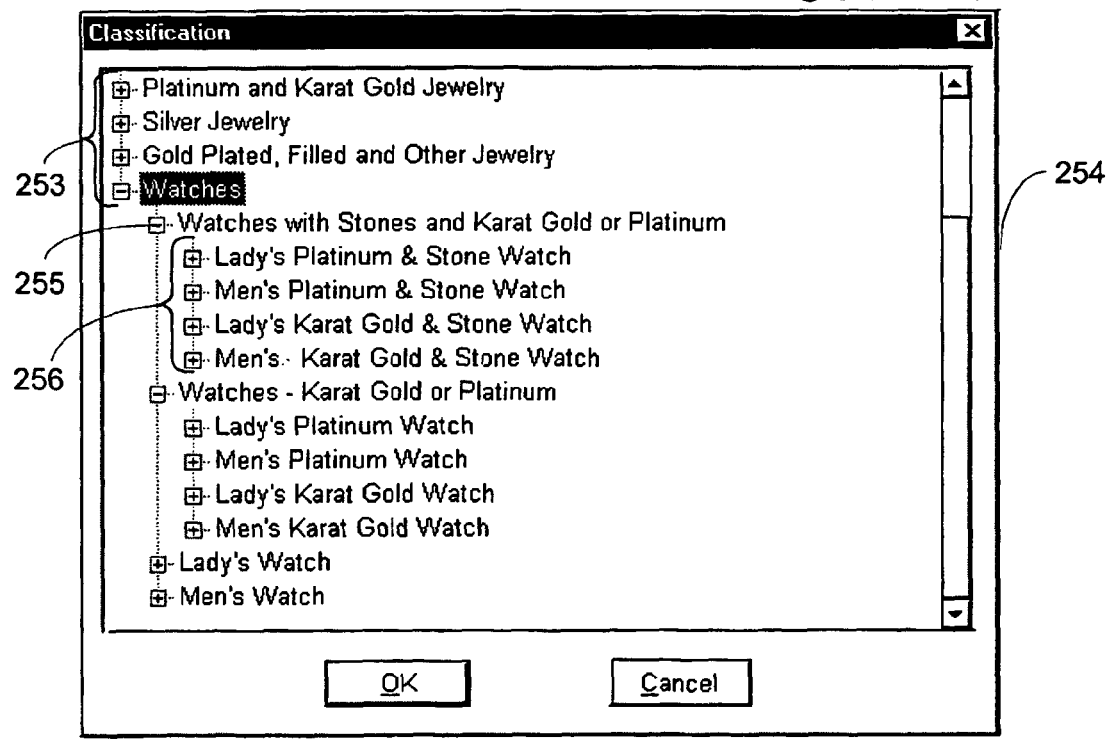
Figure 8E:
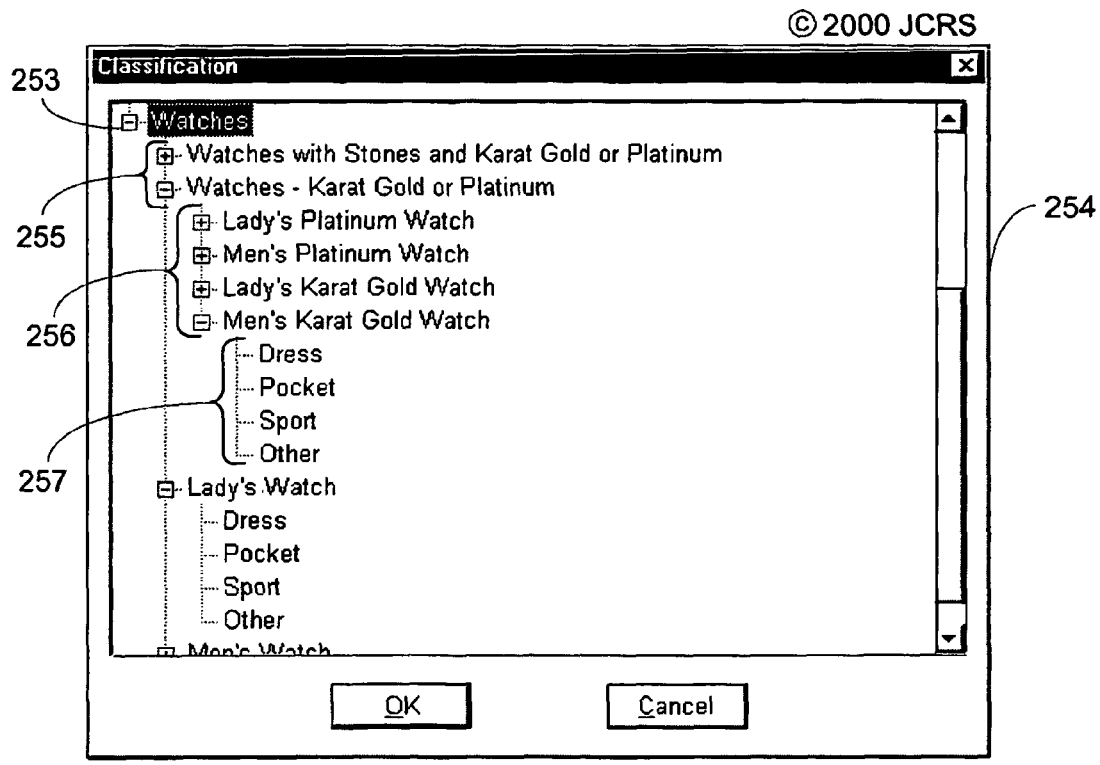
Figure 8F:
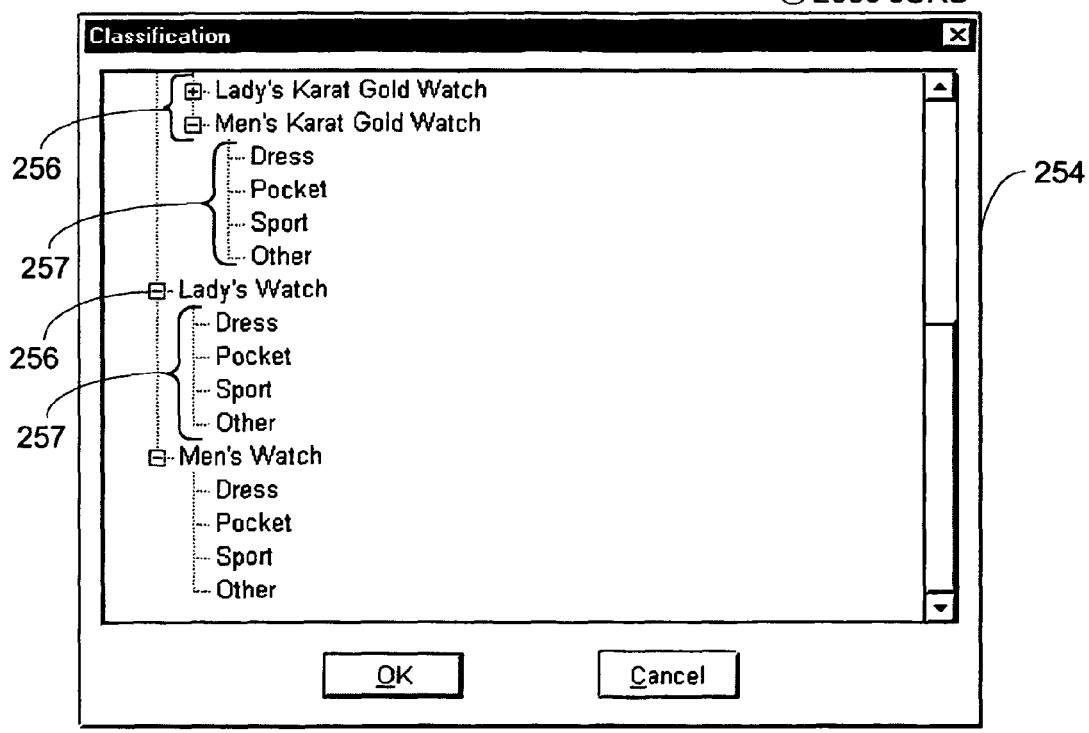

In FIGS. 8e through 8ff a representative list of four-level item classifications is illustrated. A variety of characterizations for loose goods, strung pearls, diamonds, gems, watches, and other jewelry are provided. The list is appropriate for use, for example, in connection with jewelry insurance appraisals.

Figure 9:
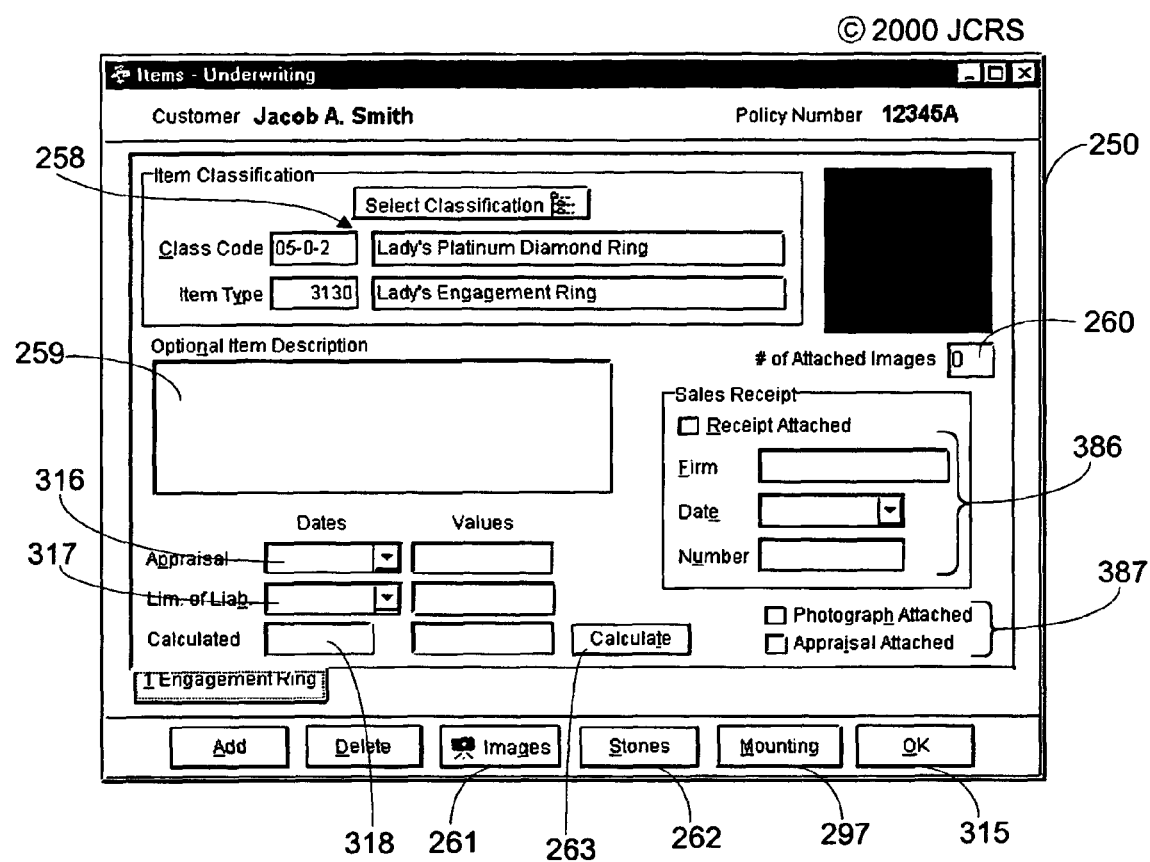

Selection of a primary characteristic 253 "mounted diamond," secondary characteristic 255 "platinum diamond jewelry," tertiary characteristic 256 "lady's ring" and fourth-level "engagement" results in the screen of FIG. 9 with the indications shown in fields 258. Selection of option 251 "Add" and subsequent entry of data has enabled options 385 "delete", 261 "images", 262 "stones", and 297 "mounting," as well as data fields 259, 386, and 387, and "calculate" option 263. Activation of these fields and options is indicated by highlighting thereof, as may be seen by comparison of FIGS. 7 and 9.

Computer, digital, or other images of the item may optionally be associated with the description by selection of option 261, with the number of associated image files being shown in field 260; and optional additional textual description may be entered in field 259.

If the "calculate" instruction 263 is selected at this point, the program returns a relatively unrefined estimate of value or optionally refuses to provide any value at all, and gives an indication that essential information is missing. The user is prompted to continue by selecting option 262 "stones", which results in the presentation of screen 270 in FIG. 10a.

Figure 10A:
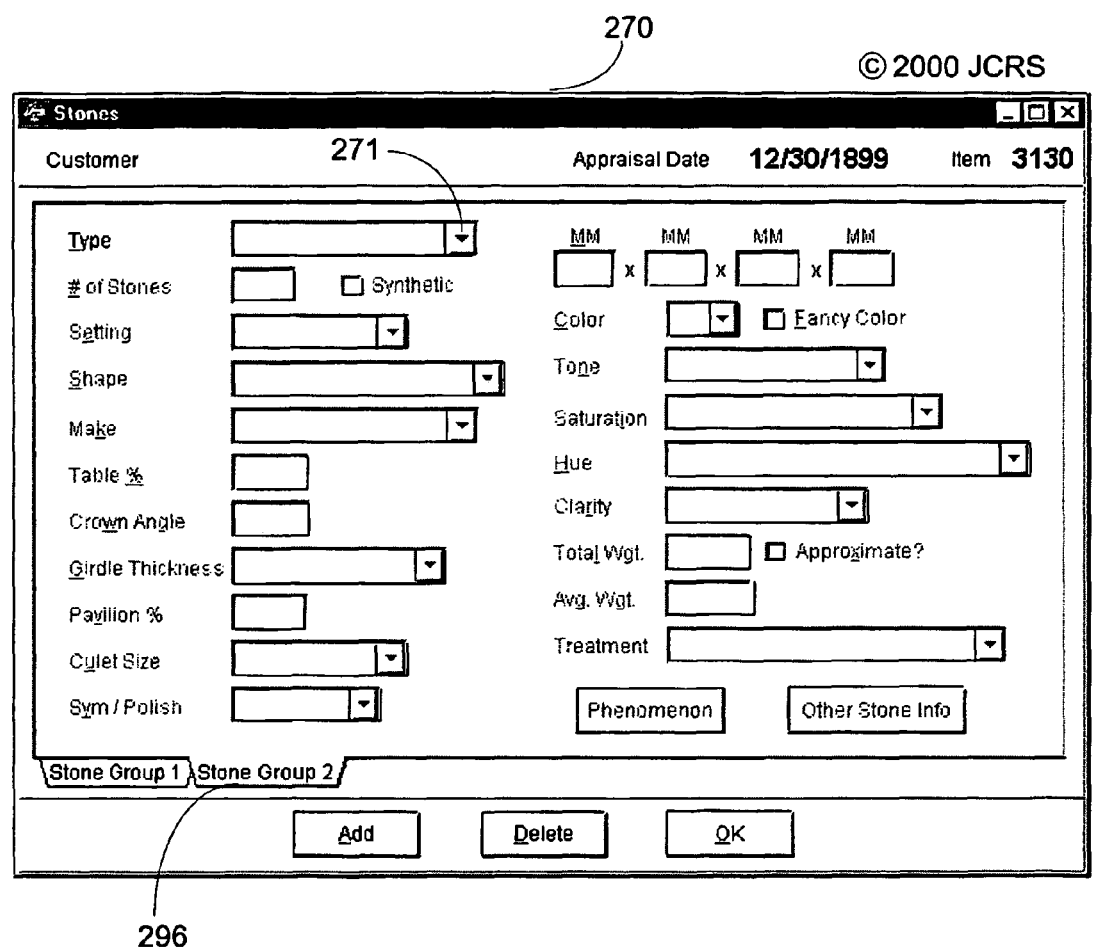
Figure 10B:
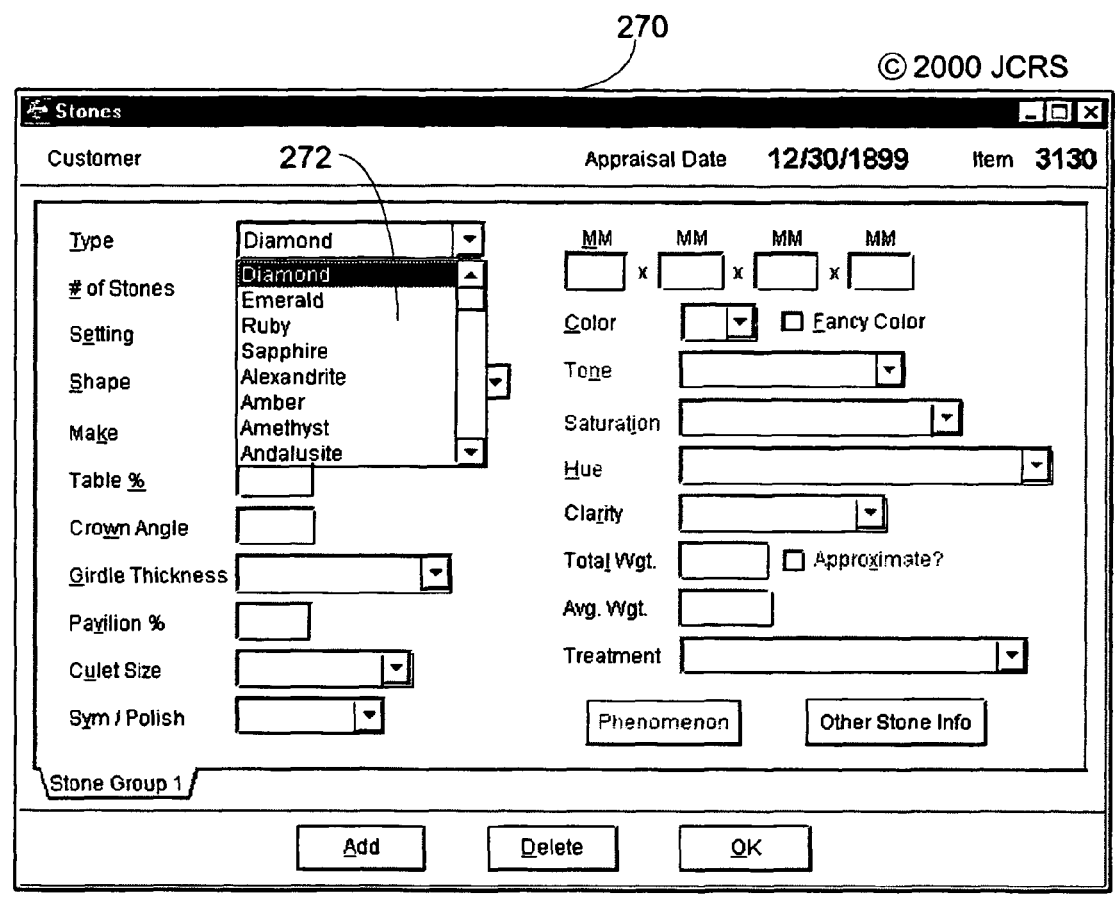
Figure 10C:
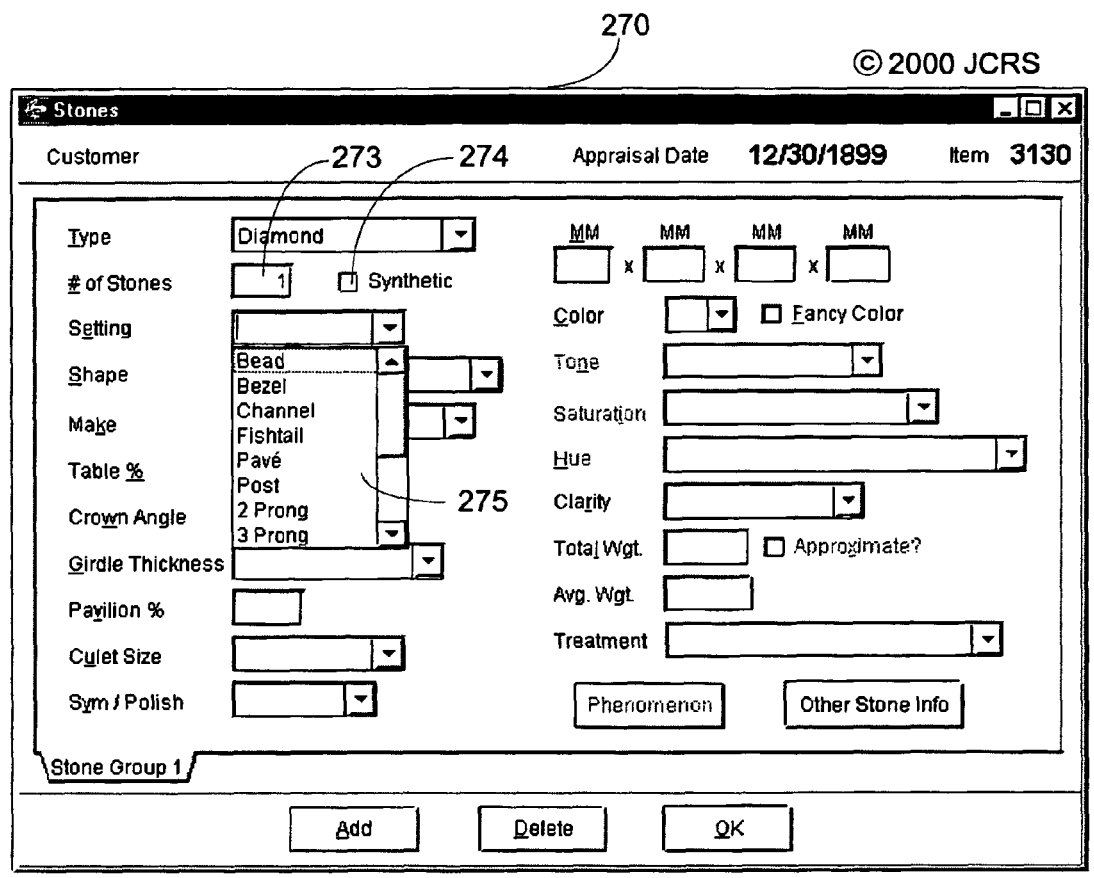
Figure 10D:
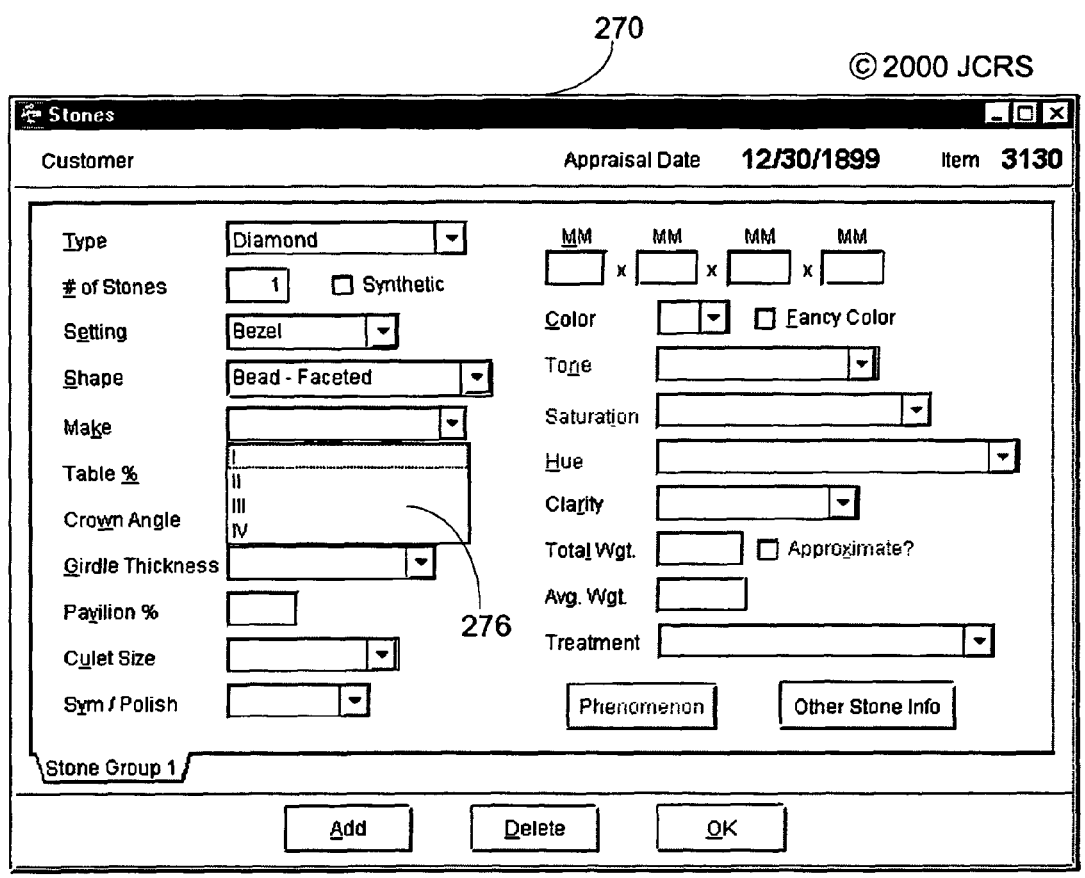
Figure 10E:
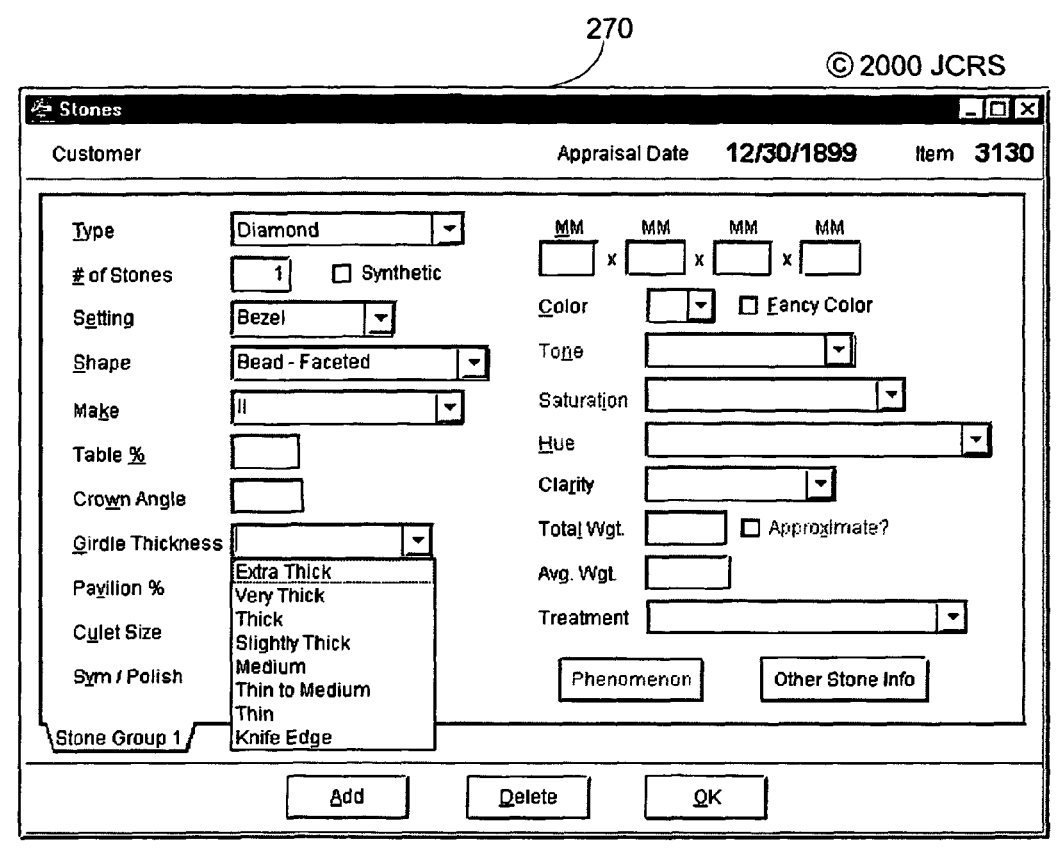

Screen 270 presents a number of "pull-down" menus 271, which provide and activate options for entry of various stone types and characteristics, including stone types 272 (Compare option and field highlighting in FIGS. 10a and 10b). Upon designation of a stone type the user is asked (FIG. 10c) to enter the number of such stones present on the piece in field 273 and to indicate at 274 whether the stones are synthetic. Setting options are provided in menu field 275. A selection of makes is offered in menu field 276 of FIG. 10d. Optional Table percentages 277 and crown angles 278 are elicited with girdle thickness 279 as shown in FIG. 10e.

Figure 10F:
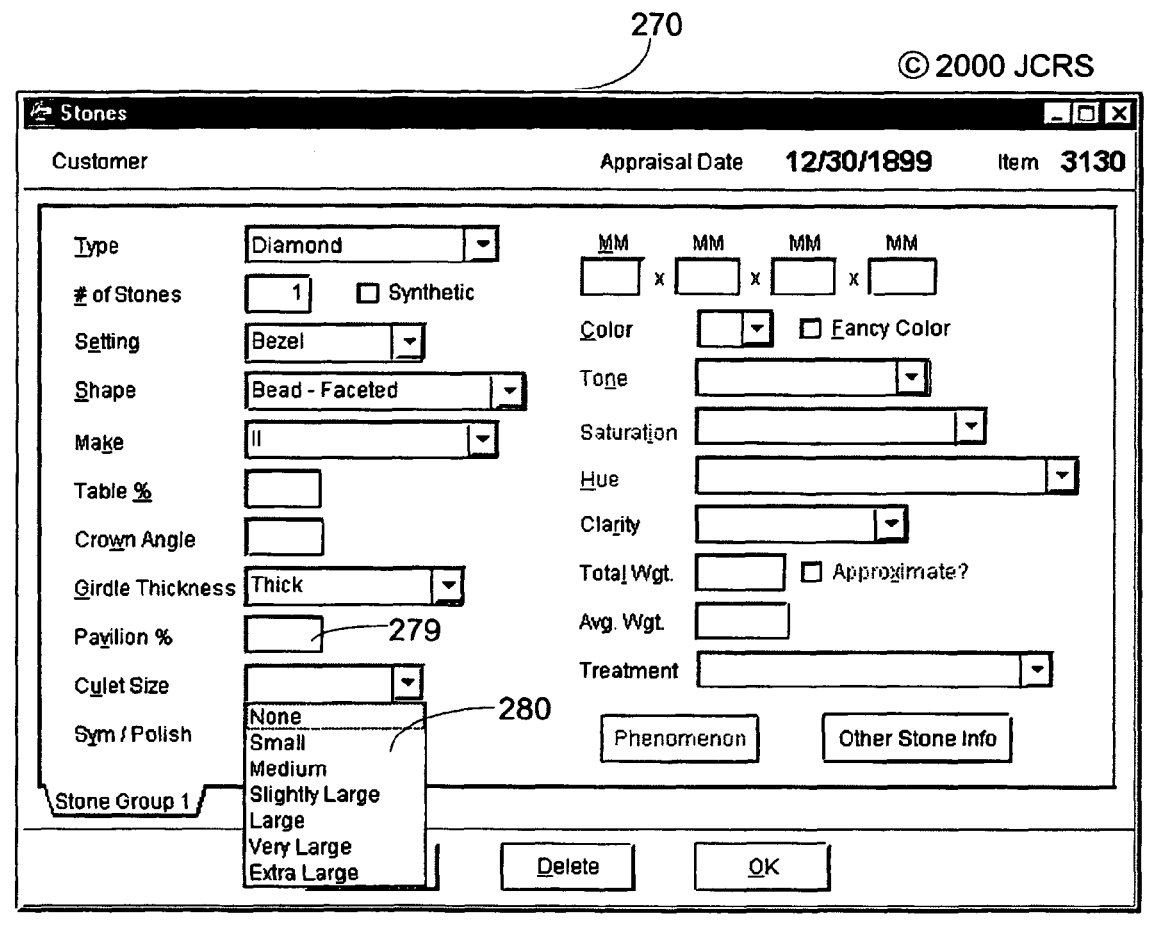
Figure 10G:
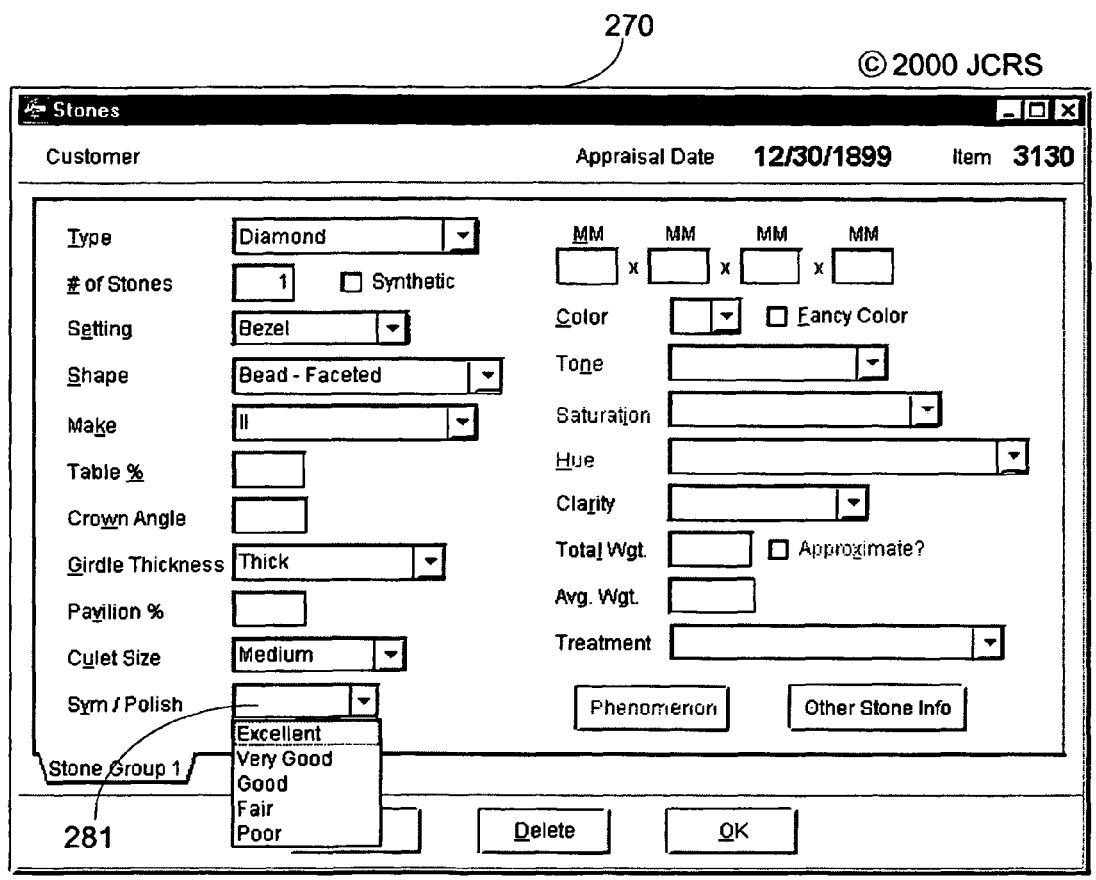
Figure 10H:
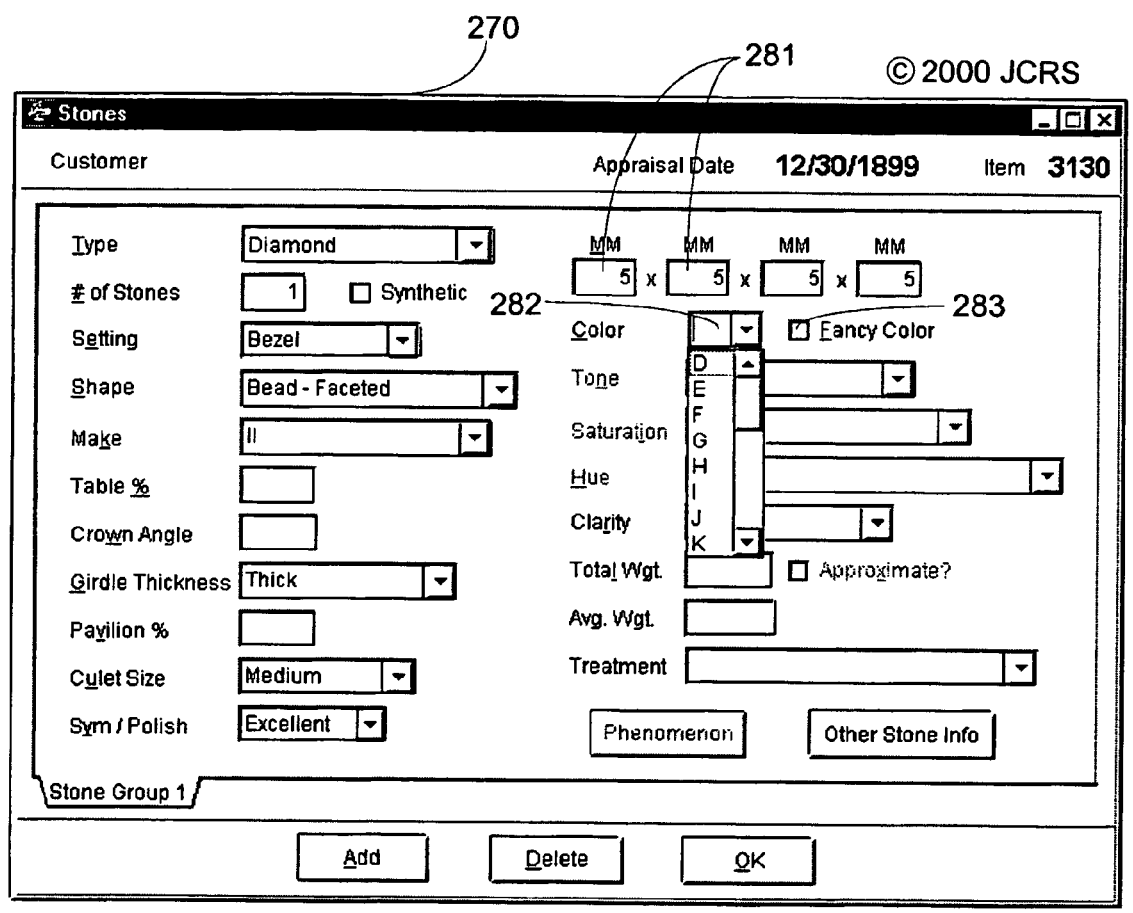
Figure 10I:
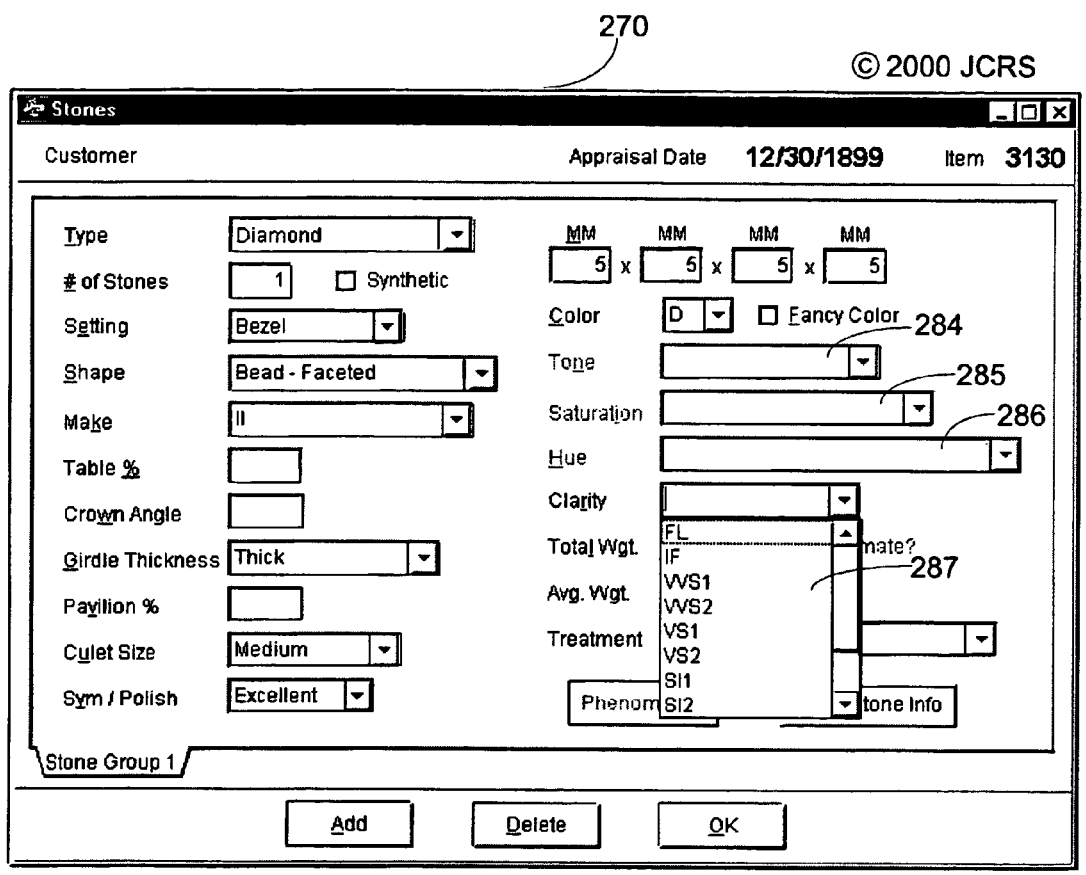

Optional pavilion percentages 279 and cutlet sizes 280 are elicited in FIG. 10f. In FIG. 10g symmetry and polish quality 281 is elicited, and in FIG. 10h the user is prompted for stone dimensions 281 and color 282; an optional indication of special or fancy color is permitted at 283. In FIG. 10i the user is prompted for stone tone 284, saturation level 285, hue 286 (note again that depending upon the selection of various options various other options are enabled or disabled appropriately) and clarity 287.

Figure 10J:
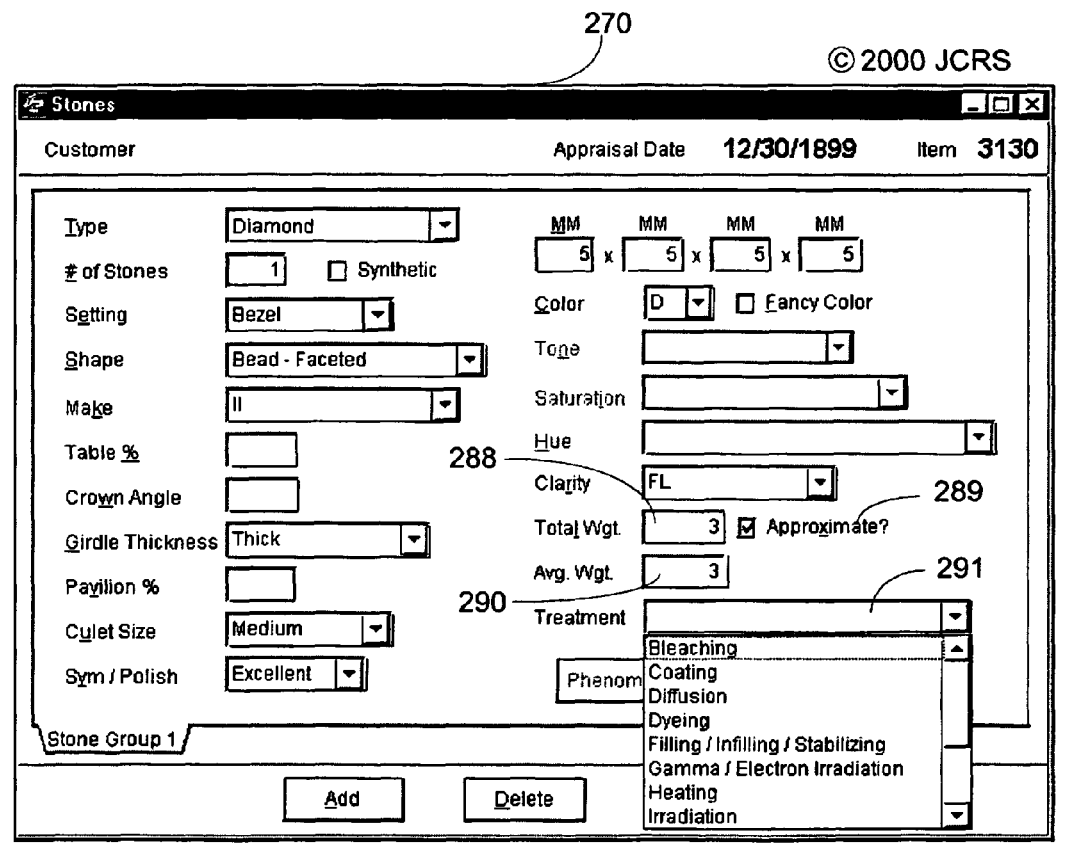

Field 288 in FIG. 10j prompts the user for total stone weight, with an indication at 289 of whether the weight is approximate and a prompt for average weight indication at 290 for multiple-stone rings. In field 291 the user is invited to select a treatment.

Figure 10K:
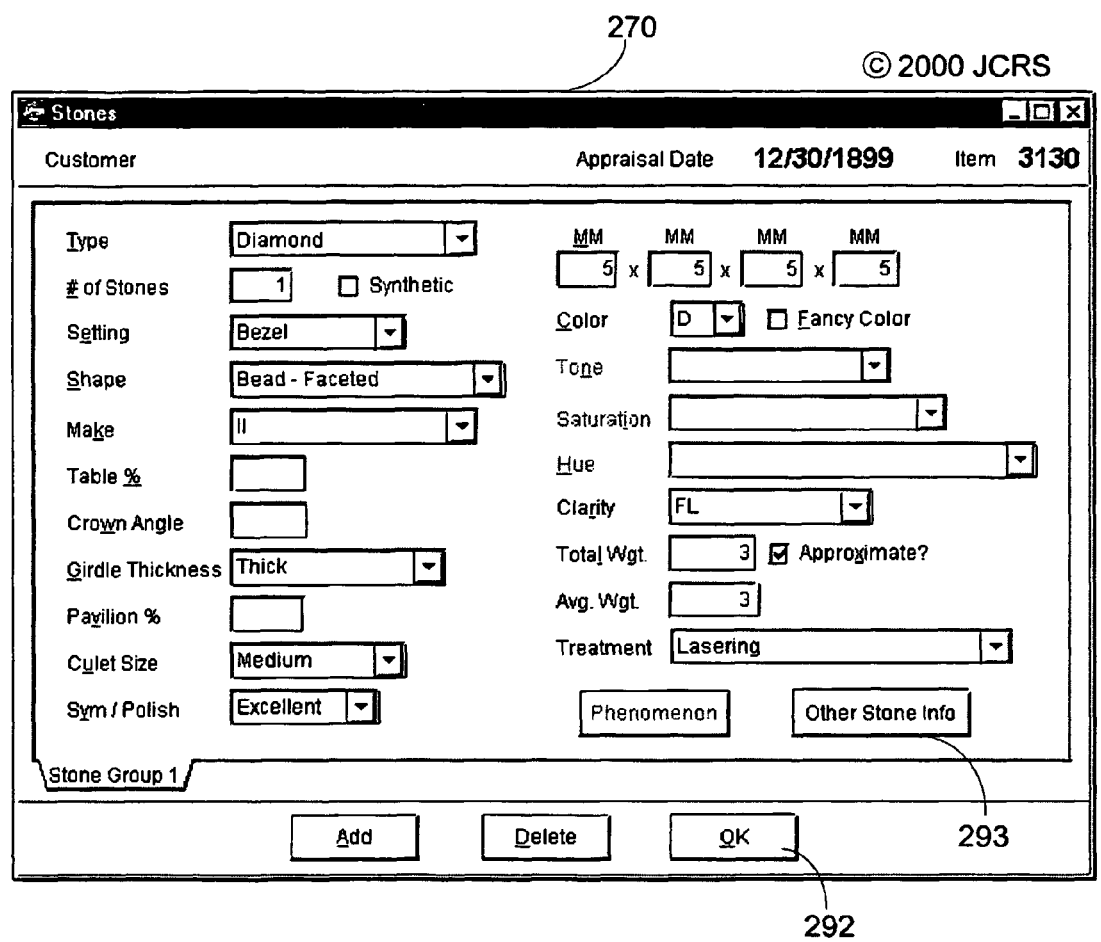
Figure 10L:
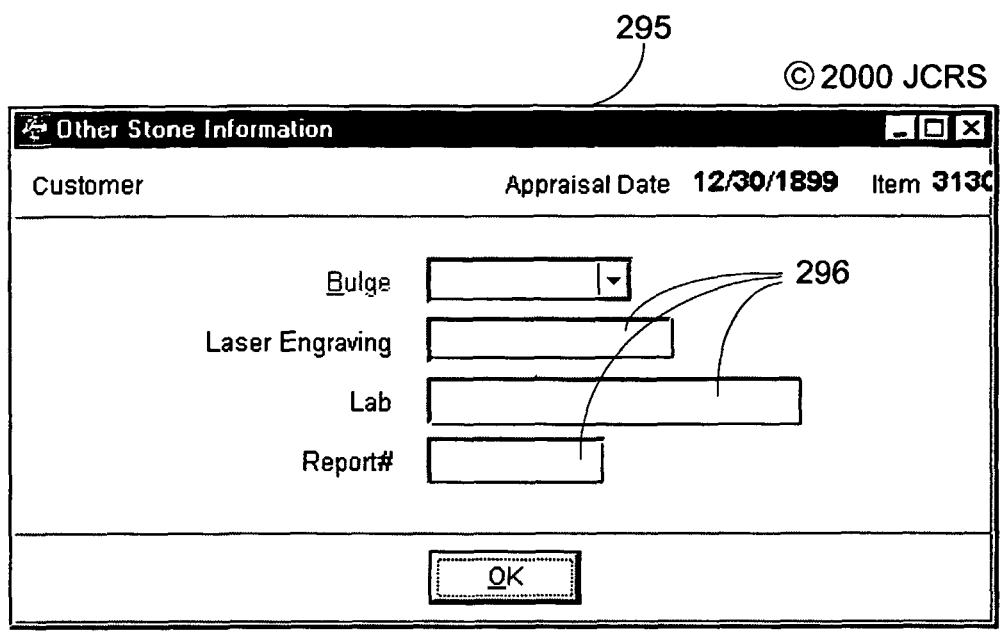

Miscellaneous information may be entered by selecting option 293 of FIG. 10k, which causes screen 295 of FIG. 10l to be presented fields 296 appropriate to previous selections active. A completed stone description screen 270 is shown in FIG. 10k. Selection of option 292 returns the user to item screen 250 of FIG. 9. Again, if any of the information solicited by screen 270 is omitted and an appraisal is requested, a value can be determined and reported with an indication of the quality of the appraisal.

Optionally the entry of one set of stone groups activates an option 296 for entry of additional stone groups in FIG. 10a. Jewelry items containing more than on type of stone are not uncommon; this option helps facilitate accurate appraisal of such pieces.

Figure 11A:
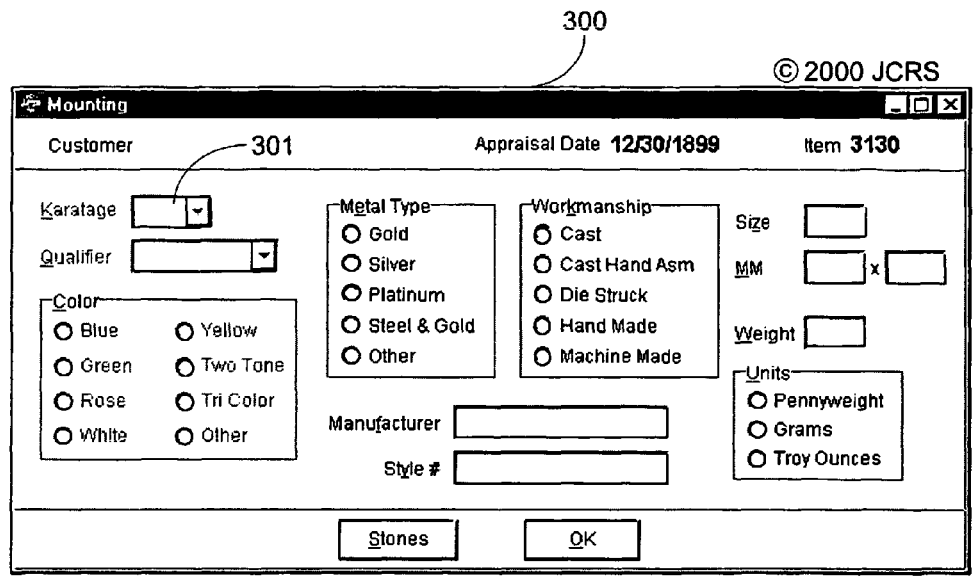
Figure 11B:
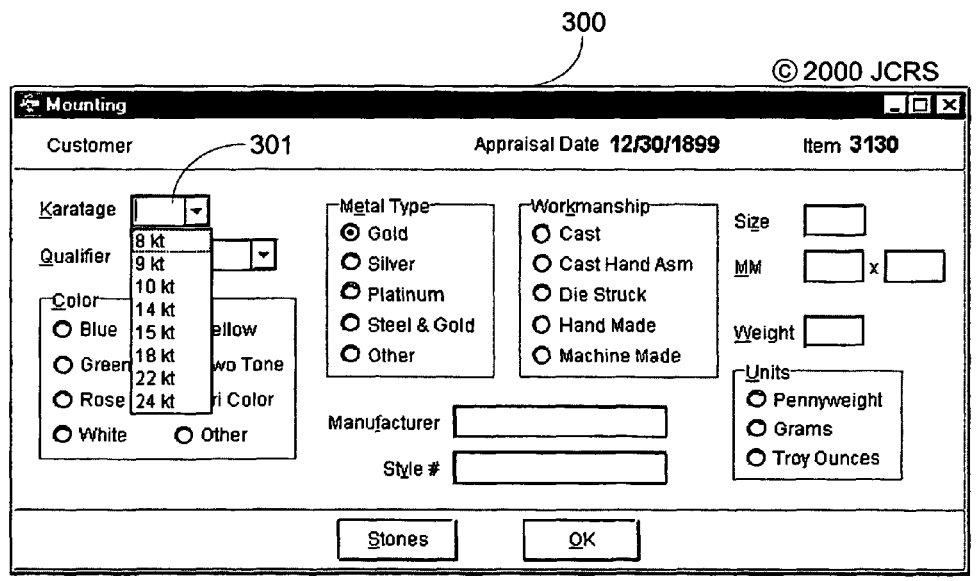
Figure 11C:
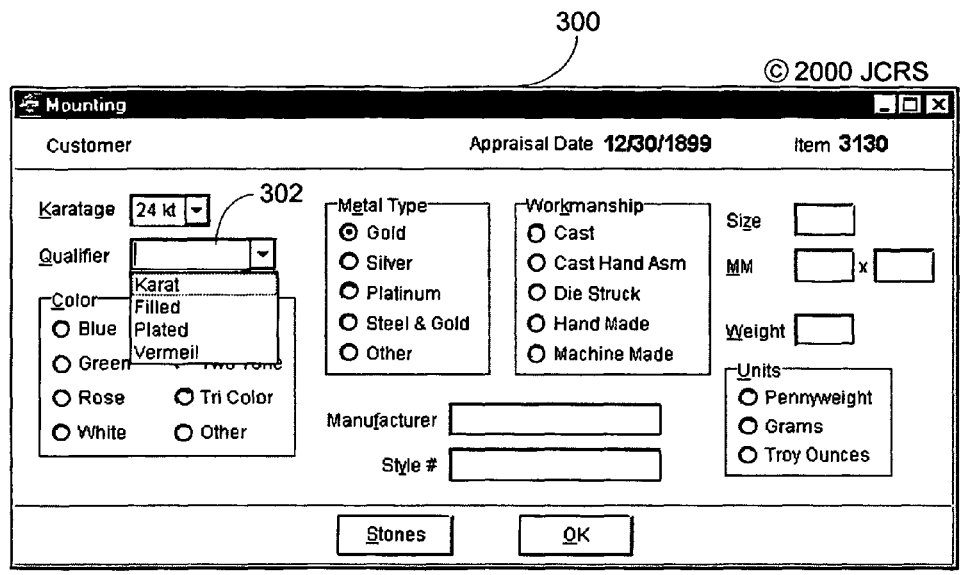
Figure 11D:
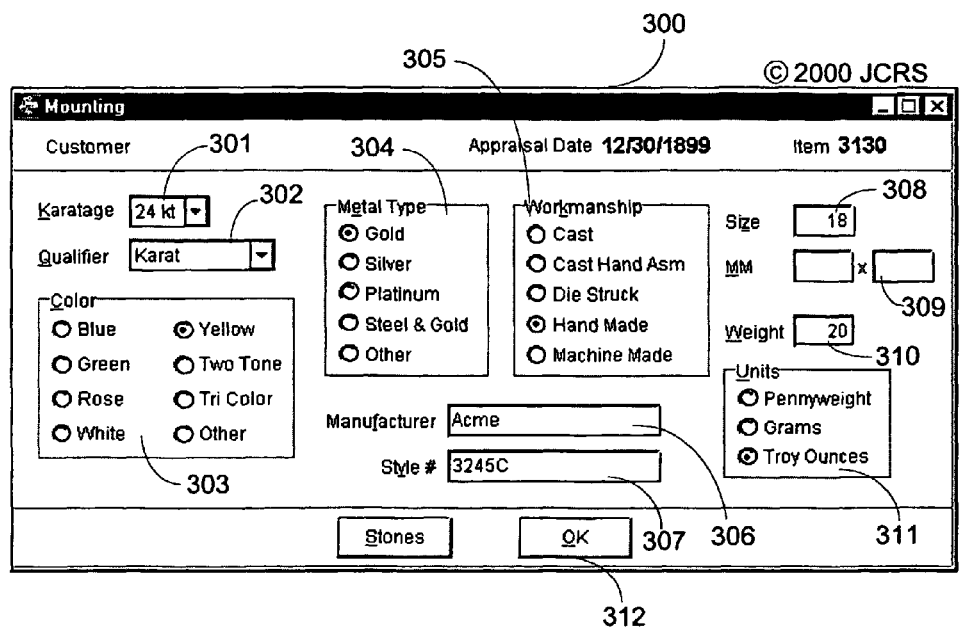

Description of the item is continued in FIG. 9 through selection of option 297, "mounting", which results in presentation of screen 300 of FIG. 11a. Screen 300 comprises a number of data entry fields, several of which are optionally activated dependent upon previous choices such as mounting material (which includes relative purity item 301 in FIG. 11b, which comprises an optional pull-down menu of weight ranges); optional purity description qualifiers 302 of FIG. 11c; color 303; metal type 304; workmanship 305; manufacturer 306; manufacturer's style code 307; size 308; dimensions 309; weight value 310; and weight units 311 in FIG. 11d. Selection of option 312 with the selection/entry of values shown returns the user to screen 250 of FIG. 9.

Figure 12:
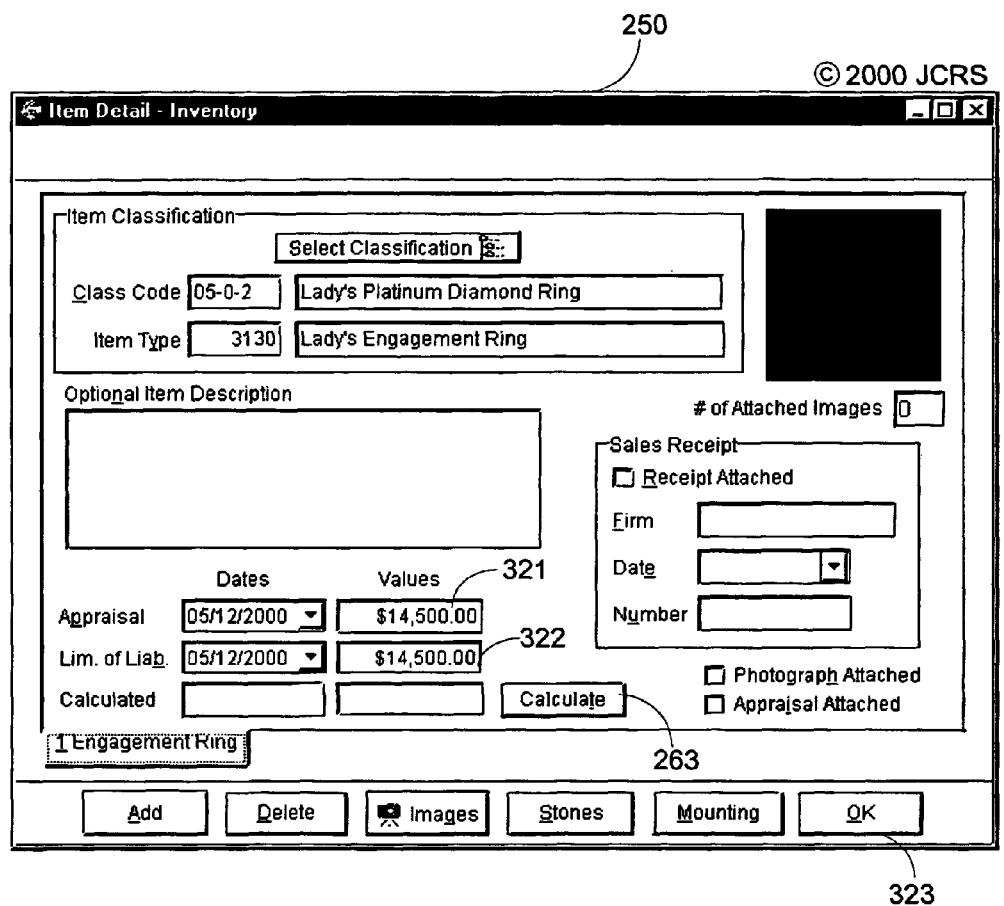
Figure 13:
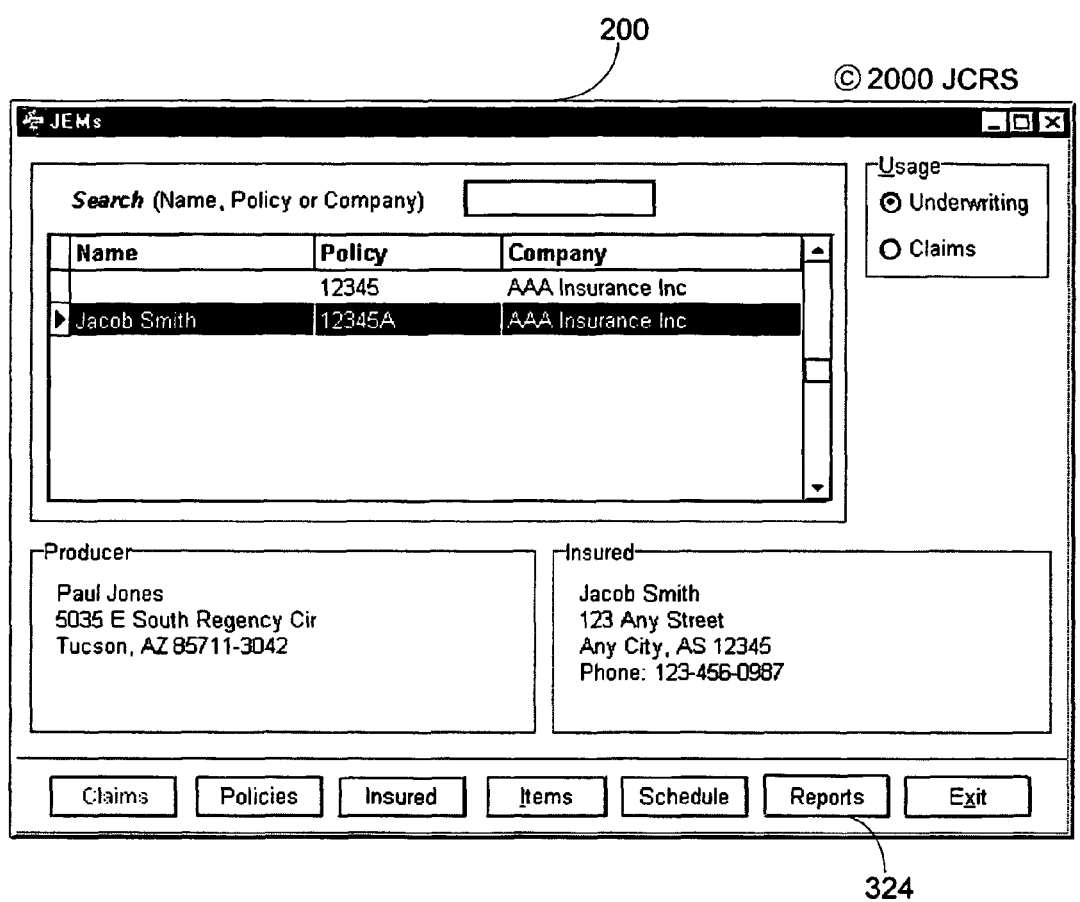
Figure 14:
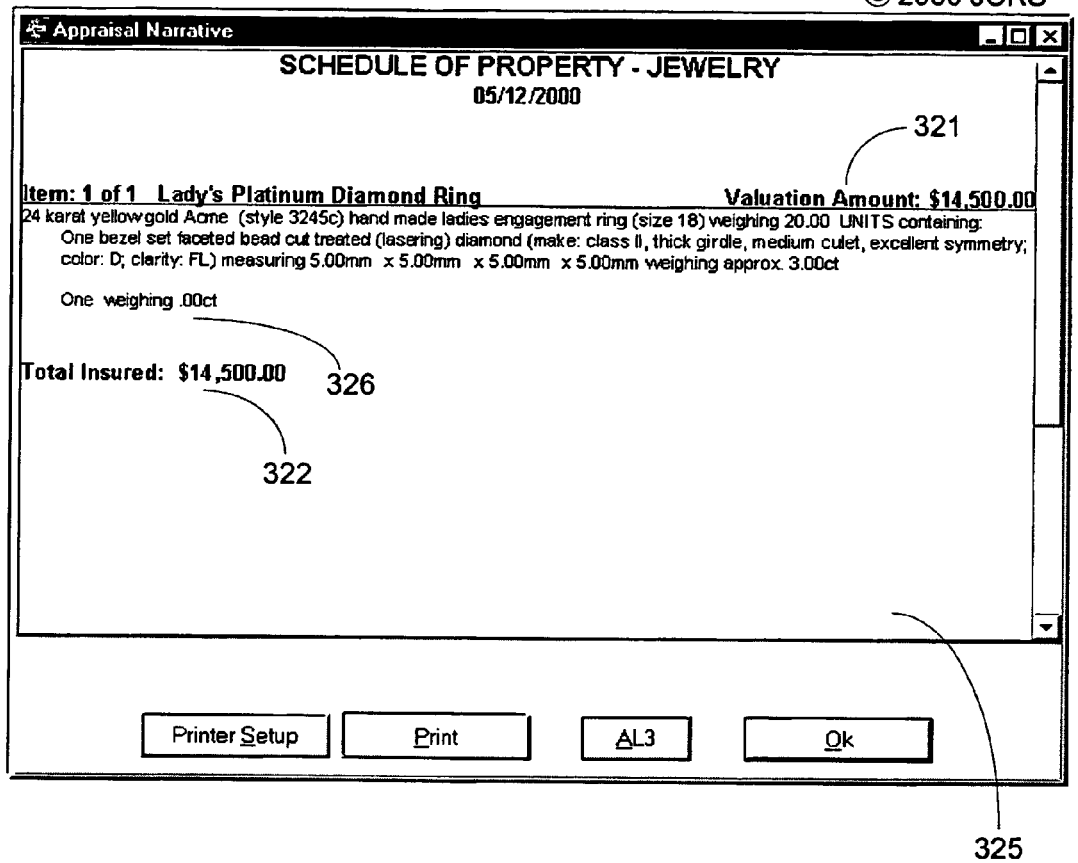

When an entered description of the item is complete, option 315 of FIG. 9 is selected. Appraisal date 316, limit of liability date 317, and calculation date 318 are entered, and option 320 "calculate" is selected, in screen 250. If any relevant description elements are missing the user is prompted to enter them, or default values are provided in accordance with the description herein, and an appraisal value is calculated in accordance with the disclosure, based on the description entered by the user and any default data supplied by the JEMS program. The appraisal is given as of the requested appraisal date 316. The resulting appraisal value is indicated at field 321, and a limit of liability at field 322, as shown in FIG. 12. Selection of option 323 results in presentation of screen 200 of FIG. 13, upon which selection of option 324 "reports" results in presentation of report 325 of FIG. 14, which may be printed, presented on the screen, written to a file, or any combination thereof.

Report 325 comprises appraisal value 321 and liability limit value 322, together with complete description 326 of the item as provided by the user. In cases in which an incomplete description in provided by the user, report 325 further comprises a report of the quality of the appraisal and optionally a caution regarding use thereof.

Figures 15, 16:
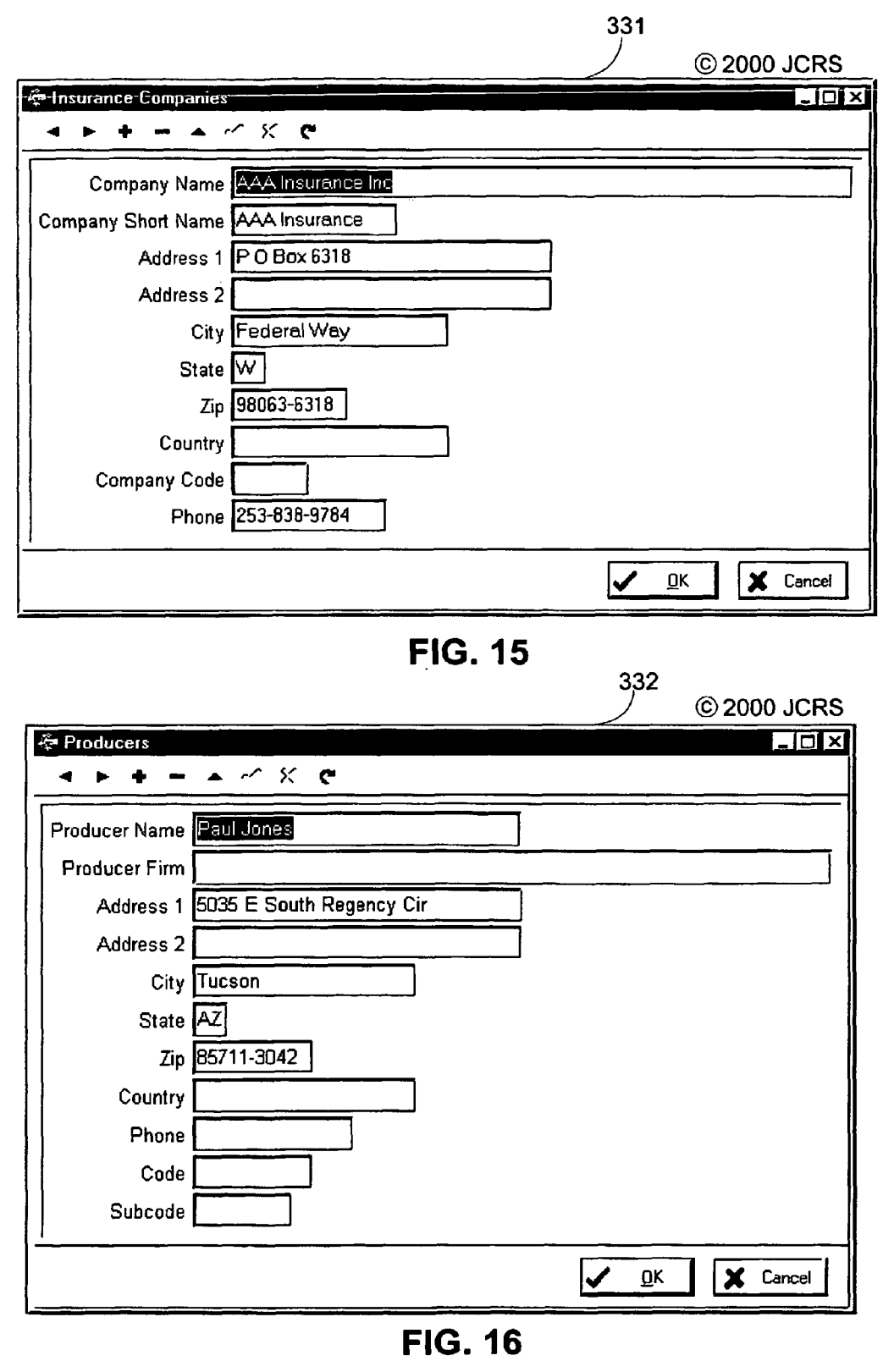

Optional screens 331 and 332 generated in response to selection of options 234 or 235 in FIG. 4 re shown in FIGS. 15 and 16, respectively. Each of the screens solicits information for the addition of additional relevant entities. Screen 331 facilitates entry of information related to an insurance company; screen 332 information related to a producer.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modification are intended to be included within the scope of the invention.

What is claimed is:

1. A computer-based method for appraising valuable items, the method comprising:

receiving, from a first network computer, a description of a first valuable item, the description of the first valuable item including one or more required descriptive elements and one or more non-required descriptive elements;

determining, using one or more processors, that the description of the first valuable item is missing a required descriptive element;

in response to the determination that the description of the first valuable item is missing the required descriptive element;

setting an appraisal quality flag to red, sending a request to the first network computer to provide the missing required descriptive element, receiving, from the first network computer, the missing required descriptive element, setting, in response to the reception of the missing required descriptive element, the appraisal quality flag to green, retrieving a first set of item values associated with the first valuable item, determining, using the one or more processors and based on the description of the first valuable item and the first set of item values, an appraisal value for the first valuable item, and forwarding the appraisal value for the first valuable item and the green appraisal quality flag;

receiving, from a second network computer, a description of a second valuable item, the description of the second valuable item including one or more required descriptive elements and one or more non-required descriptive elements;

determining, using the one or more processors, that the description of the second valuable item is missing a non-required descriptive element;

in response to the determination that the description of the second valuable item is missing the non-required descriptive element;

determining, using the one or more processors, a default value for the missing non-required descriptive element, determining, using the one or more processors, that the missing non-required descriptive element is not critical, setting, in response to the determination that the missing non-required element is not critical, the appraisal quality flag to yellow, and forwarding the yellow appraisal quality flag;

receiving, from a third network computer, a description of a third valuable item, the description of the third valuable item including one or more required descriptive elements and one or more non-required descriptive elements;

determining, using the one or more processors, that the description of the third valuable item is missing a non-required descriptive element; and in response to the determination that the description of the third valuable item is missing the non-required descriptive element:

determining, using the one or more processors, a default value for the missing non-required descriptive element, determining, using the one or more processors, that the missing non-required descriptive element is not significant, setting, in response to the determination that the missing non-required element is not significant, the appraisal quality flag to green, retrieving a second set of item values associated with the third valuable item, determining, using the one or more processors and based on the description of the third valuable item and the second set of item values, an appraisal value for the third valuable item, and forwarding the appraisal value for the third valuable item and the green appraisal quality flag.

2. The method according to claim 1, wherein the first valuable item includes a stone and a mounting, and the description of the first valuable item comprises a stone type, a stone weight, a stone color, a stone clarity, a stone cut, a mounting material, a mounting weight, and a mounting style.

3. The method according to claim 1, further comprising receiving an appraisal purpose from the first network computer, wherein determining the appraisal value for the first valuable item is based on the description of the first valuable item, the appraisal purpose, and the first set of item values.

4. The method according to claim 3, wherein the appraisal purpose is an insurance appraisal or a sale.

5. The method according to claim 1, wherein the default value is determined from one or more data tables.

6. The method according to claim 1, wherein the first set of item values are stored in one or more data tables.

7. The method according to claim 1, further comprising receiving a request from the first network computer to determine the default value for the missing non-required descriptive element.

8. The method according to claim 1, wherein forwarding the appraisal value for the first valuable item and the green appraisal quality flag comprises forwarding the appraisal value for the first valuable item, the green appraisal quality flag, and the description of the first valuable item to the first network computer.

9. The method according to claim 1, wherein the first network computer, the second network computer, and the third network computer are the same.

10. The method according to claim 1, wherein the first network computer, the second network computer, and the third network computer are different.

11. The method according to claim 1, wherein determining the default value for the missing non-required descriptive element comprises accessing a default value data set.

12. The method according to claim 1, wherein retrieving the first set of item values associated with the first valuable item comprises determining an item class of the first valuable item based on the description of the first valuable item.

13. The method according to claim 1, wherein retrieving the second set of item values associated with the third valuable item comprises determining an item class of the third valuable item based on the description of the third valuable item.

14. The method according to claim 1, wherein forwarding the appraisal value for the third valuable item and the green appraisal quality flag comprises forwarding the appraisal value for the third valuable item, the green appraisal quality flag, and the description of the third valuable item to the third network computer.

15. The method according to claim 1, wherein the valuable items are jewelry items.

16. A system for appraising valuable items, the system comprising one or more processors connected to at least one storage device, the system being configured to:

receive, from a first network computer, a description of a first valuable item, the description of the first valuable item including one or more required descriptive elements and one or more non-required descriptive elements;

determine that the description of the first valuable item is missing a required descriptive element;

in response to the determination that the description of the first valuable item is missing the required descriptive element:

set an appraisal quality flag to red, send a request to the first network computer to provide the missing required descriptive element, receive, from the first network computer, the missing required descriptive element, set, in response to the reception of the missing required descriptive element, the appraisal quality flag to green, retrieve a first set of item values associated with the first valuable item, determine, based on the description of the first valuable item and the first set of item values, an appraisal value for the first valuable item, and forward the appraisal value for the first valuable item and the green appraisal quality flag;

receive, from a second network computer, a description of a second valuable item, the description of the second valuable item including one or more required descriptive elements and one or more non-required descriptive elements;

determine, that the description of the second valuable item is missing a non-required descriptive element;

in response to the determination that the description of the second valuable item is missing the non-required descriptive element:

determine a default value for the missing non-required descriptive element, determine that the missing non-required descriptive element is not critical, set, in response to the determination that the missing non-required element is not critical, the appraisal quality flag to yellow, and forward the yellow appraisal quality flag;

receive, from a third network computer, a description of a third valuable item, the description of the third valuable item including one or more required descriptive elements and one or more non-required descriptive elements;

determine that the description of the third valuable item is missing a non-required descriptive element; and in response to the determination that the description of the third valuable item is missing the non-required descriptive element:

determine a default value for the missing non-required descriptive element, determine that the missing non-required descriptive element is not significant, set, in response to the determination that the missing non-required element is not significant, the appraisal quality flag to green, retrieve a second set of item values associated with the third valuable item, determine, based on the description of the third valuable item and the second set of item values, an appraisal value for the third valuable item, and forward the appraisal value for the third valuable item and the green appraisal quality flag.

17. A non-transitory computer readable medium storing a computer program for appraising valuable items, the computer program comprising one or more code segments that, when executed, cause one or more processors to:

receive, from a first network computer, a description of a first valuable item, the description of the first valuable item including one or more required descriptive elements and one or more non-required descriptive elements;

determine that the description of the first valuable item is missing a required descriptive element;

in response to the determination that the description of the first valuable item is missing the required descriptive element:

set an appraisal quality flag to red, send a request to the first network computer to provide the missing required descriptive element, receive, from the first network computer, the missing required descriptive element, set, in response to the reception of the missing required descriptive element, the appraisal quality flag to green, retrieve a first set of item values associated with the first valuable item, determine, based on the description of the first valuable item and the first set of item values, an appraisal value for the first valuable item, and forward the appraisal value for the first valuable item and the green appraisal quality flag;

receive, from a second network computer, a description of a second valuable item, the description of the second valuable item including one or more required descriptive elements and one or more non-required descriptive elements;

determine, that the description of the second valuable item is missing a non-required descriptive element;

in response to the determination that the description of the second valuable item is missing the non-required descriptive element:

determine a default value for the missing non-required descriptive element, determine that the missing non-required descriptive element is not critical, set, in response to the determination that the missing non-required element is not critical, the appraisal quality flag to yellow, and forward the yellow appraisal quality flag;

receive, from a third network computer, a description of a third valuable item, the description of the third valuable item including one or more required descriptive elements and one or more non-required descriptive elements;

determine that the description of the third valuable item is missing a non-required descriptive element; and in response to the determination that the description of the third valuable item is missing the non-required descriptive element:

determine a default value for the missing non-required descriptive element, determine that the missing non-required descriptive element is not significant, set, in response to the determination that the missing non-required element is not significant, the appraisal quality flag to green, retrieve a second set of item values associated with the third valuable item, determine, based on the description of the third valuable item and the second set of item values, an appraisal value for the third valuable item, and forward the appraisal value for the third valuable item and the green appraisal quality flag.

* * * * *